United States Patent
De Ridder

(10) Patent No.: US 9,656,077 B2
(45) Date of Patent: May 23, 2017

(54) COMBINATION OF TONIC AND BURST STIMULATIONS TO TREAT NEUROLOGICAL DISORDERS

(71) Applicant: ADVANCED NEUROMODULATION SYSTEMS, INC., Plano, TX (US)

(72) Inventor: Dirk De Ridder, Dunedin (NZ)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 15/254,432

(22) Filed: Sep. 1, 2016

(65) Prior Publication Data

US 2016/0367811 A1 Dec. 22, 2016

Related U.S. Application Data

(63) Continuation of application No. 14/288,199, filed on May 27, 2014, now Pat. No. 9,462,398, which is a continuation of application No. 13/751,998, filed on Jan. 28, 2013, now Pat. No. 8,774,927, which is a continuation of application No. 12/109,098, filed on Apr. 24, 2008, now Pat. No. 8,364,273.

(60) Provisional application No. 60/913,613, filed on Apr. 24, 2007.

(51) Int. Cl.
*A61N 1/36* (2006.01)
*A61N 1/372* (2006.01)
*G06F 19/00* (2011.01)
*A61N 1/08* (2006.01)
*H04R 25/00* (2006.01)
*A61N 1/00* (2006.01)
*A61N 1/05* (2006.01)

(52) U.S. Cl.
CPC .......... *A61N 1/36071* (2013.01); *A61N 1/08* (2013.01); *A61N 1/361* (2013.01); *A61N 1/36067* (2013.01); *A61N 1/36096* (2013.01); *A61N 1/36178* (2013.01); *A61N 1/37264* (2013.01); *G06F 19/3481* (2013.01); *H04R 25/75* (2013.01); *A61N 1/00* (2013.01); *A61N 1/0551* (2013.01)

(58) Field of Classification Search
None
See application file for complete search history.

(56) References Cited

U.S. PATENT DOCUMENTS

| | | | | |
|---|---|---|---|---|
| 5,031,618 A | * | 7/1991 | Mullett | A61B 5/1116 607/46 |
| 6,535,767 B1 | * | 3/2003 | Kronberg | A61N 1/326 607/51 |
| 2008/0065158 A1 | * | 3/2008 | Ben-Ezra | A61N 1/36071 607/2 |
| 2008/0243204 A1 | * | 10/2008 | Uthman | A61N 1/36071 607/45 |

* cited by examiner

Primary Examiner — Kennedy Schaetzle

(57) ABSTRACT

The present application relates to a new stimulation design which can be utilized to treat neurological conditions. The stimulation system produces a combination of burst and tonic stimulation which alters the neuronal activity of the predetermined site, thereby treating the neurological condition or disorder.

4 Claims, 8 Drawing Sheets

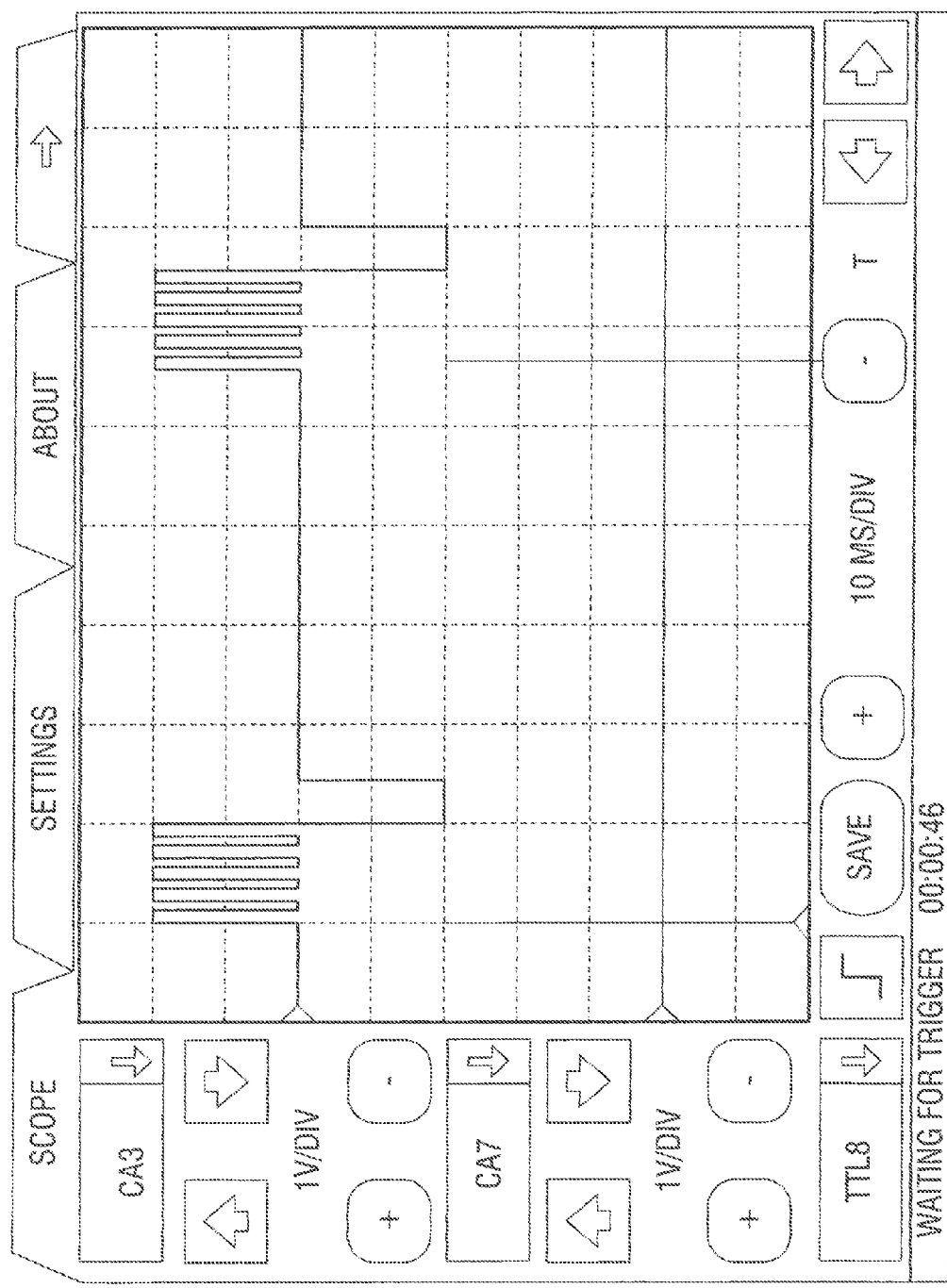

COMBINATION OF TONIC AND BURST STIMULATIONS TO TREAT NEUROLOGICAL DISORDERS

CROSS-REFERENCE TO RELATED APPLICATIONS

This application is a continuation of U.S. application Ser. No. 14/288,199, filed May 27, 2014, which is a continuation of U.S. application Ser. No. 13/751,998, filed Jan. 28, 2013, now U.S. Pat. No. 8,774,927, which is a continuation of U.S. application Ser. No. 12/109,098, filed Apr. 24, 2008, now U.S. Pat. No. 8,364,273, which claims the benefit of U.S. Provisional Application No. 60/913,613, filed Apr. 24, 2007, the disclosures of which are fully incorporated herein by reference for all purposes.

BACKGROUND

The present application relates to a stimulation system and method that utilizes combined burst and tonic stimulation parameters to treat neurological conditions and/or disorders.

Different firing modes or frequencies occur in the brain and/or other neuronal tissue, for example tonic firing and burst firing (irregular or regular burst firing). Such firing modes can be utilized for normal processing of information, however, alteration of the firing modes, may also lead to pathology.

For example, certain neurological conditions are associated with hyperactivity of the brain and can be traced to a rhythmic burst firing or high frequency tonic firing (e.g., tinnitus, pain, and epilepsy). Other conditions can be associated with an arrhythmic burst firing or a desynchronized form of tonic and burst firing (e.g., movement disorders and hallucinations).

During the past decade, neuromodulation systems have been used to modulate various areas of the brain, spinal cord, or peripheral nerves (See, for example, U.S. Pat. Nos. 6,671,555; 6,690,974). These types of systems utilize tonic forms of electrical stimulation. Recently burst transcranial magnetic stimulation (TMS) at theta frequencies has been developed (Huang et al., 2005). Theta burst TMS has been shown to produce an effect on motor and visual cortex by suppressing excitatory circuits after a short application period of only 20-190 s (Huang et al., 2005; Di Lazzaro et al., 2005; Franca et al., 2006). However, there is not a system that utilizes both types of electrical stimulation.

Thus, the inventor is the first to describe a neuromodulation design or stimulation parameters in which the stimulation parameters produce a combination of burst stimulation and tonic stimulation to override or alter the pathological and/or physiological stimulation to treat a neurological condition.

SUMMARY

In one representative embodiment, a method of neurostimulation comprises generating, by an implantable pulse generator, a stimulus that is a burst stimulus that comprises a plurality of groups of spike pulses in combination with one or more single spike pulses; providing the burst stimulus from the implantable pulse generator to a medical lead; and applying the burst stimulus to nerve tissue of the patient via one or several electrodes of the medical lead.

In further embodiments, a tonic stimulus is delivered within the inter-burst interval, for example, the tonic spike stimulus may be fixed in relation to the preceding burst stimulus or the subsequent burst stimulus. Yet further, the timing of the burst stimulus may be fixed in relation to the preceding tonic spike stimulus or subsequent the tonic spike stimulus.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

For a more complete understanding of the present application, reference is now made to the following descriptions taken in conjunction with the accompanying drawing, in which:

FIGS. 1A-1B illustrate exemplary combinations of burst and tonic stimuli. FIG. 1A shows the tonic stimulation surrounding the burst stimulation. FIG. 1B shows tonic and burst stimulation can be combined on the same poles or center tone.

DETAILED DESCRIPTION

I. Definitions

Figure 1B:
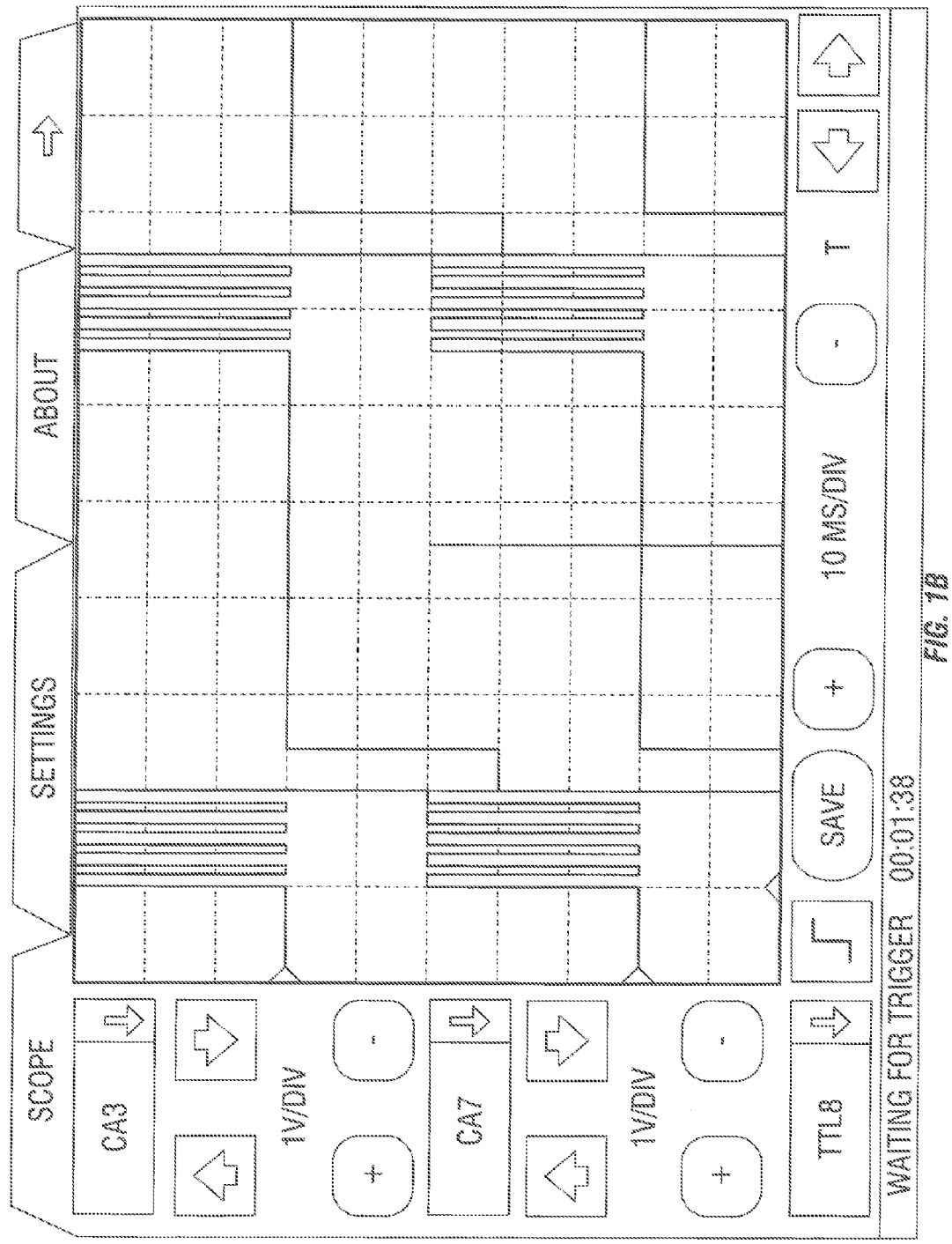

Unless defined otherwise, technical and scientific terms used herein have the same meaning as commonly understood by one of ordinary skill in the art. For purposes of the present application, the following terms are defined below.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

As used herein, the term "in communication" refers to the stimulation lead being adjacent, in the general vicinity, in close proximity, or directly next to or directly on the predetermined stimulation site. Thus, one of skill in the art understands that the lead is "in communication" with the predetermined site if the stimulation results in a modulation of neuronal activity. The predetermined site may be selected from the group consisting of the peripheral neuronal tissue or central neuronal tissue. Central neuronal tissue includes, but is not limited to brain tissue, brainstem, spinal tissue.

As used herein, the use of the term "dorsal column" refers to conducting pathways in the spinal cord that are located in the dorsal portion of the spinal cord between the posterior horns, and which comprises afferent somatosensory neurons. The dorsal column is also known as the posterior funiculus.

As used herein, the use of the words "epidural space" or "spinal epidural space" is known to one with skill in the art, and refers to an area in the interval between the dural sheath and the wall of the spinal canal.

As used herein the term "modulate" refers to the ability to regulate positively or negatively neuronal activity. Thus, the term modulate can be used to refer to an increase, decrease, masking, altering, overriding or restoring of neuronal activity.

As used herein, the terms "spike", "action potential", and "pulse", all refer to a rapid rise and fall of voltage or current. One skilled in the art realizes that the term action potential generally refers to a spike or pulse that is produced by neurons. One skilled in the art also recognizes that the term action potential can also be expanded to include the spiking of cells in other excitable tissues. The terms spike and pulse may refer to action potentials produced by neurons or other excitable cells. Alternatively, the terms spike and pulse may refer to voltage or current generated by a pulse generator device. Those of skill in the art are aware that the spikes generated by a pulse generator device can be either bipolar or monopolar or a combination of both bipolar and monopolar. The terms "inter-spike interval" or "inter-pulse interval" refer to the period of time between two action potentials, spikes, or pulses. However, one of skill in the art also realizes that naturally occurring spikes do not necessarily occur at a fixed rate; this rate can be variable. In such cases an average inter-spike interval may be used to define the average period of time between two action potentials.

As used herein, the term "tonic" as well as the phrases "tonic firing", "tonic spike", "tonic pulse", or "tonic mode" refers to any process in which individual spikes occur with relatively long inter-spike intervals. Tonic firing modes may be defined operatively as having spikes that occur with sufficiently long interspike intervals that significant temporal summation of cellular depolarizations does not occur.

As used herein, the term "burst" as well as the phrases "burst firing", "burst spikes", or "burst mode" refers to a rapid succession of two or more neuronal action potentials in the approximate frequency range of (100-1000 Hz) (Beurrier et al., 1999). Similarly, a burst spike may be described as a spike that is preceded or followed by another spike within a short time interval of approximately (0.5 μsec-10 msec) (Matveev, 2000). Those skilled in the art recognize that a burst can refer to a plurality of groups of spike pulses. A burst is a train of action potentials that, possibly, occurs during a 'plateau' or 'active phase', followed by a period of relative quiescence called the 'silent phase' (Nunemaker, Cellscience Reviews Vol 2 No. 1, 2005.) A burst may be operatively defined as a period in time in which two or more spikes occur relatively rapidly, such that the spikes summate in a non-linear fashion. The period of time between the beginning of a burst and the end of the same said burst is defined as the "intra-burst interval". The period of time between two bursts is known as the "inter-burst interval". The inter-burst interval may not be affected by the presence of any number of tonic spikes located anywhere within a series of two or more bursts. One skilled in the art is also aware that burst firing can also be referred to as phasic firing, rhythmic firing (Lee 2001), pulse train firing, oscillatory firing and spike train firing, all of these terms used herein are interchangeable.

As used herein, "burst stimulation" refers to pulses generated by a pulse generator that is similar to burst firing of action potentials within neural tissue. Specifically, burst stimulation includes multiple discrete bursts with each burst comprising multiple pulses or spikes. Burst stimulation may occur from a plateau or elevated pulse amplitude applied by the pulse generator. Also, a hyper-polarizing or other preconditioning pulse may precede the burst. A charge balancing pulse or pulses may be applied within the burst or at the end of the burst. Within a burst of electrical pulses, the electrical pulses are separated from each adjacent pulse by an inter-pulse interval. The intra-burst inter-pulse interval can be about 0.5 microseconds to about 10 milliseconds. However, one of skill in the art also realizes that the intra-burst spike rate does not necessarily occur at a fixed rate; this rate can be variable.

As used herein, the term "neuronal" refers to a cell which is a morphologic and functional unit of the brain, brainstem, spinal cord, and peripheral nerves.

As used herein, the term "peripheral neuronal tissue" refers to any neuronal tissue associated with a nerve root, root ganglion, or peripheral nerve that is outside the brain and the spinal cord. Peripheral neuronal tissue also includes cranial nerves. It includes the autonomous nervous system, inclusive of (ortho-)sympathetic and parasympathetic system. Furthermore, those of skill in the art realize that peripheral neuronal tissue also includes stimulating the peripheral nervous tissue associated with a dermatome.

As used herein, the term "dermatome" refers to the area of skin innervated by a single dorsal root. One of skill in the art realizes that the boundaries of dermatomes are not distinct and in fact overlap because of overlapping innervations by adjacent dorsal roots. Dermatomes are divided into sacral (S), lumbar (L), thoracic (T) and cervical (C). Yet further, as used herein, the term "dermatome" includes all the neuronal tissues located within the region or adjacent to the dermatome area, for example, it may include any peripheral nerve, or any cervical nerve root (e.g., C1, C2, C3, C4, C5, C6, C7 and C8) that may innervate the dermatome. For example, the C2/C3 dermatome area may comprise any peripheral nerve (e.g., the occipital nerve (the greater, the lesser, the third and the suboccipital nerve), the great auricular nerve, the transverse cervical nerve, the supraclavicular nerve, spinal accessory nerve, phrenic nerve, dorsal scapular nerve) that arises from the C2 or C3 nerve root.

As used herein, the term "central neuronal tissue" refers to neuronal tissue associated with the brain, spinal cord or brainstem.

As used herein, the term "neurology" or "neurological" refers to conditions, disorders, and/or diseases that are associated with the nervous system. The nervous system comprises two components, the central nervous system, which is composed of the brain and the spinal cord, and the peripheral nervous system, which is composed of ganglia and the peripheral nerves that lie outside the brain and the spinal cord. One of skill in the art realizes that the nervous system may be linguistically separated and categorized, but functionally the system is interconnected and interactive. Yet further, the peripheral nervous system is divided into the autonomic system (parasympathetic and sympathetic), the somatic system and the enteric system. Thus, any condition, disorder and/or disease that effect any component or aspect of the nervous system (either central or peripheral) are referred to as a neurological condition, disorder and/or disease. As used herein, the term "neurological" or "neurology" encompasses the terms "neuropsychiatric" or "neuropsychiatry" and "neuropsychological" or "neuropsychology". Thus, a neurological disease, condition, or disorder includes, but is not limited to tinnitus, epilepsy, depression, anxiety, Parkinson's Disease, autonomic dysfunctions, etc.

As used herein, the term "neuropsychiatry" or "neuropsychiatric" refers to conditions, disorders and/or diseases that relate to both organic and psychic disorders of the nervous system.

As used herein, the term "neuropsychological" or "neuropsychologic" or neuropsychology refers to conditions, disorders and/or disease that relate to the functioning of the brain and the cognitive processors or behavior.

As used herein, "spinal cord," "spinal nervous tissue associated with a vertebral segment," "nervous tissue associated with a vertebral segment" or "spinal cord associated with a vertebral segment or level" includes any spinal nervous tissue associated with a vertebral level or segment. Those of skill in the art are aware that the spinal cord and tissue associated therewith are associated with cervical, thoracic, and lumbar vertebrae. As used herein, C1 refers to cervical vertebral segment 1, C2 refers to cervical vertebral segment 2, and so on. T1 refers to thoracic vertebral segment 1, T2 refers to thoracic vertebral segment 2, and so on. L1 refers to lumbar vertebral segment 1, L2 refers to lumbar vertebral segment 2, and so on, unless otherwise specifically noted. In certain cases, spinal cord nerve roots leave the bony spine at a vertebral level different from the vertebral segment with which the root is associated. For example, the T11 nerve root leaves the spinal cord myelum at an area located behind vertebral body T8-T9 but leaves the bony spine between T11 and T12.

As used herein, the term "stimulate" or "stimulation" refers to electrical, chemical, magnetic, thermal and/or other such stimulation that modulates the predetermined neuronal sites.

As used herein, the term "treating" and "treatment" refers to modulating predetermined neuronal sites (central neuronal tissue and/or peripheral neuronal tissue) so that the subject has an improvement in the disease or condition, for example, beneficial or desired clinical results. For purposes of this application, beneficial or desired clinical results include, but are not limited to, alleviation of symptoms, diminishment of extent of disease, stabilized (e.g., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

II. Clinical Relevance

A. Tinnitus

Introduction

Tinnitus is an auditory phantom percept (Jastreboff, 1990; Muhlnickel et al., 1998) related to reorganization (Muhinickel et al., 1998) and hyperactivity (Eggermont and Roberts, 2004) of the auditory system. The auditory system consists of two main parallel pathways supplying auditory information to the cerebral cortex: the topographically organized lemniscal (classical) system, and the non-topographic extralemniscal (non-classical) system. The classical pathways use the ventral thalamus, the neurons of which project to the primary auditory cortex whereas the non-classical pathways use the medial and dorsal thalamic nuclei that project to the secondary auditory cortex and association cortices, thus bypassing the primary cortex (Møller, 2003). While neurons in the classical pathways only respond to one modality of sensory stimulation, many neurons in the non-classical pathway respond to more than one modality. Neurons in the ventral thalamus fire in a tonic or semi-tonic mode while neurons in the medial and dorsal thalamus fire in bursts (He and Hu, 2002; Hu et al., 1994). The non-classical pathways receive their input from the classical pathways, which means that the ascending auditory pathways are a complex system of at least two main parallel systems that provide different kinds of processing and which interact with each other in a complex way. Both systems provide sensory input to the amygdala through a long cortical route, and in addition, the non-classical pathways provide subcortical connections to the lateral nucleus of the amygdala from dorsal thalamic nuclei (LeDoux, 1993).

Studies in humans have indicated that some patients with tinnitus have an abnormal activation of the non-classical auditory system (Moller et al., 1992). Studies of animal models of tinnitus have shown that burst firing is increased in the non-classical system (Chen and Jastreboff, 1995; Eggermont, 2003; Eggermont and Kenmochi, 1998) and tonic firing activity is increased in the classical system Brozoski et al., 2002; Kaltenbach and Afman, 2000; Kaltenbach et al., 1998; Kaltenbach et al., 2004; Zacharek et al., 2002; Zhang and Kaltenbach, 1998). Interestingly, not only tonic firing but also burst firing is increased in neurons in the primary auditory cortex in animal models of tinnitus (Ochi and Eggermont, 1997). Studies in patients with intractable tinnitus have shown that tonic electrical stimuli of the primary and secondary auditory cortex can suppress pure tone tinnitus, but not white noise/narrow band noise tinnitus (De Ridder et al., 2006).

The inventors have tested the hypothesis that noise-like tinnitus may be caused by increased burst firing in the non-topographic (extralemniscal) system, whereas pure tone tinnitus may be the result of increased tonic firing in the topographic (lemniscal) system. Transcranial magnetic stimulation (TMS), a non-invasive tool, was shown to modulate the neuronal activity of the auditory cortex thereby modulating the perception of tinnitus (De Ridder et al., 2005; De Ridder et al., 2007a; Eichhammer et al., 2003; Kleinjung et al., 2005; Londero et al., 2006; Plewnia et al., 2003). It has been demonstrated that tonic stimulation can suppress pure tone tinnitus, but not narrow band noise, whereas burst TMS can suppress narrow band or white noise tinnitus (noise-like) (De Ridder et al., 2007b; De Ridder et al., 2007a).

In the clinical setting, cases of tinnitus are commonly complex in that the patient suffers from more than one type (i.e. pure tone, narrow band, white noise) of tinnitus in one or both ears. As such, it is unlikely that tonic mode or burst mode alone will alleviate the symptoms.

Methods and Materials

Four patients with both unilateral noise-like and pure tone (VR) tinnitus were implanted with electrodes for stimulation therapy using both tonic and burst stimulation parameters. In three patients, the electrodes (Lamitorode 44 stimulation lead available from ANS Medical, Plano, Tex., USA) were implanted in the auditory cortex, and one patient was implanted with a cervical dorsal column stimulation electrode (Lamitrode 44 stimulation lead). All patients underwent burst stimulation at 6, 18, or 40 Hz consisting of 5 spikes with 1 ms pulse width, 1 ms interspike interval in a charged balanced manner and 6, 18, or 40 Hz tonic mode interspersed between or around the bursts (FIGS. 1A and 1B). The stimuli were delivered by an 8 channel digital neurostimulator (DS8000, World Precision Instruments, Hertfordshire, England/Sarasota, Fla., USA), capable of delivering tonic and burst mode stimulation.

Figure 2:
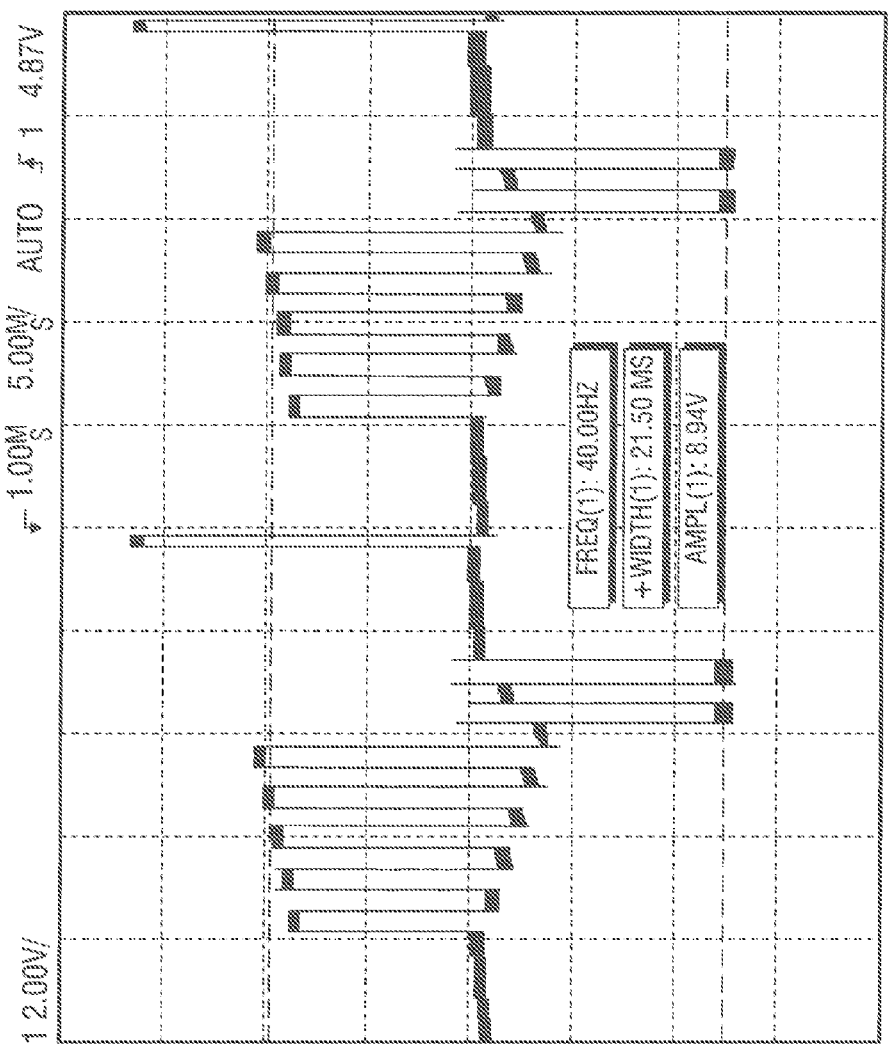
FIG. 2 illustrate an exemplary burst stimulus having ramping.

If the patients benefited from the stimulation, a commercially available IPG capable of burst mode was implanted (EON® implantable pulse generator from ANS Medical, Plano, Tex., USA), programmed with similar settings, using a custom made programmer. The only difference to the stimuli delivered with the external stimulator and the EON® implantable pulse generator, was the ramping used with the EON® implantable pulse generator (FIG. 2). The ramp was chosen to copy naturally occurring burst firing as closely as possible.

Results

The below Table 1 shows that by using a combination of tonic and burst stimulation parameters patients suffering from pure tone and noise-like tinnitus can be treated. The tonic and burst stimulation can be combined on the same poles or center tone (FIG. 1B) or surrounding the burst stimulation with tonic stimulation (FIG. 1A).

TABLE 1

| Patient | Freq Hz | Burst | Tonic | Intra-Burst Spike Rate Hz | Spikes # | Suppression of Tinnitus |
|---|---|---|---|---|---|---|
| PB (DC) | 6 | Yes | Yes | 500 | 5 | 95% |
| RM (AC) | 40 | Yes | Yes | 500 | 5 | 100% |
| DA (AC) | 40 | Yes | Yes | 500 | 5 | 90% |
| VR (AC) | 18 | Yes | Yes | 500 | 5 | 90% |

CONCLUSION

Thus, in cases of complex tinnitus combinations of burst and tonic mode stimulation were shown to effectively reduce the occurrence and severity of symptoms. Although tonic mode stimulation alone is sufficient to reduce symptom occurrence and severity in many simple cases of pure tone tinnitus, the symptoms are rarely completely abolished. Moreover, in many cases where symptoms are reduced, the effect of tonic mode stimulation is relatively short lasting and repeated treatments result in significantly reduced efficacy over time. Stimulation protocols combining burst and tonic mode stimulation are significantly more effective at reducing symptoms in patients suffering from pure tone tinnitus, the effects of a single treatment last longer, and there is no significant reduction in efficacy with repeated treatment. Yet further, the combination of burst and tonic stimulation is effective at reducing the symptoms or severity of patients that suffer from both pure tone tinnitus and noise-like tinnitus. Yet further, the combination of burst and tonic stimulation can act as an anti-habituation protocol.

Clinical Application

In view of the above results for the combination of burst and tonic stimulation, one of skill in the art can realize that such stimulation protocols can be used to treat neurological diseases/disorders having both a topographic (lemniscal system) and the non-topographic system (extralemniscal system) component. One such exemplary disease/disorder may include chronic pain. For example, typically, tonic stimulation is used to treat chronic pain. Tonic stimulation alters the topographic or lemniscal system resulting in the treatment of chronic pain. The downside to using tonic stimulation to treat chronic pain is that typically the pain may be replaced with paresthesias, which acts through the non-topographic system. Thus, an alternative to treat chronic pain without paresthesias may be to utilize a stimulation protocol that employs both burst and tonic stimulation, thereby altering both the non-topographic and the topographic system to result in treatment of chronic pain.

Yet further, another advantage of this type of combination protocol is the ability of this combination of stimulation to reduce and/or prevent anti-habituation or anti-adaptation of electrical stimulation. Those of skill in the art are aware of the problem that occurs with continual electrical stimulation in that the brain may adapt to the stimulation and the protocol is no longer effective to treat the symptoms. Thus, a combination protocol as described herein can alleviate this type of adaptation and or habituation.

III. Detailed Discussion of the Procedure

Figure 3:
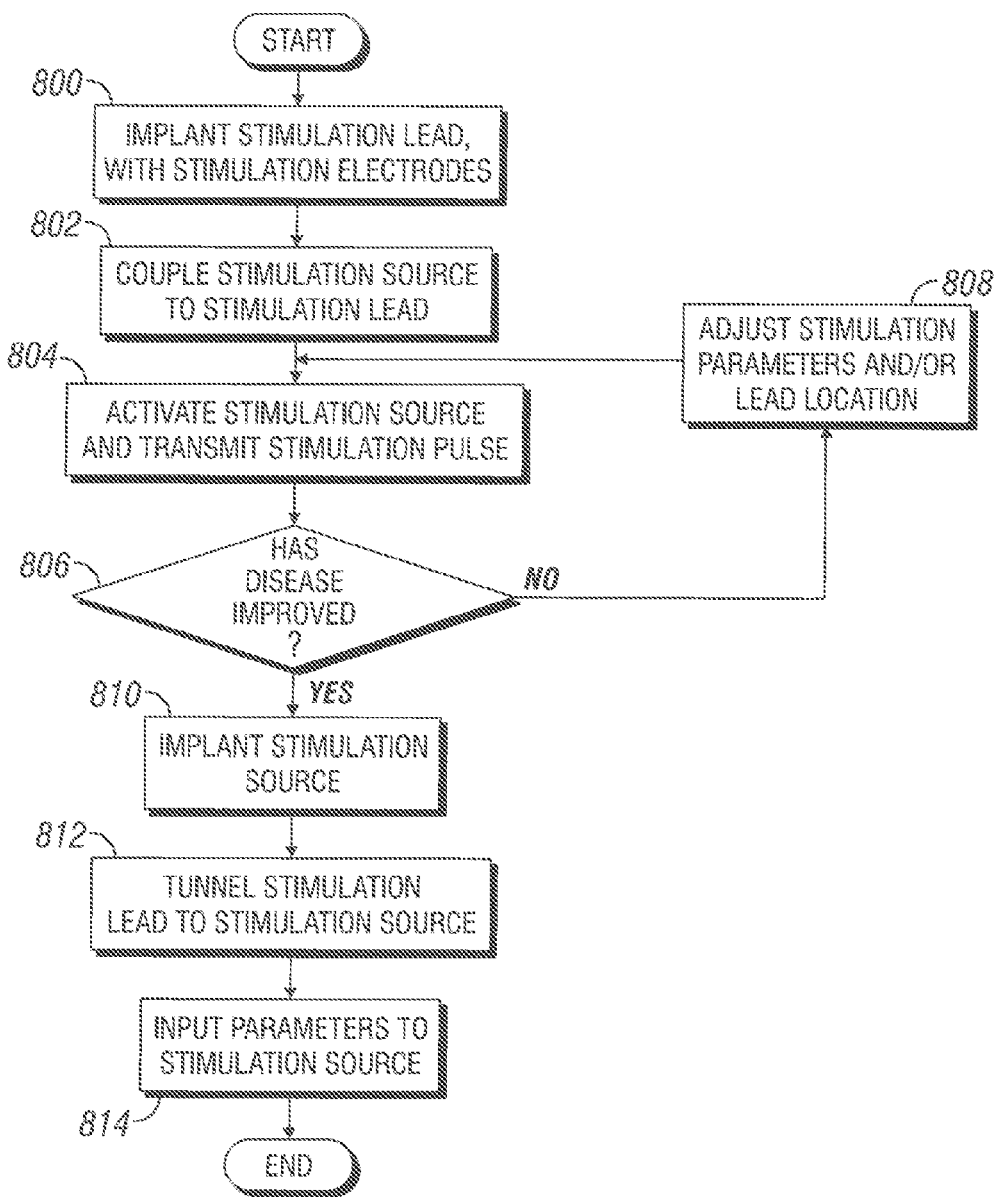
FIG. 3 is a block diagram of steps according to a method for treating a neurological disorder using a stimulation system

The following section more generally describes FIG. 3 or an example of a procedure for treatment using a combination of burst and tonic stimulation that optimizes the following four parameters; location for electrode placement, a set and/or range of stimulation protocols that can most completely eliminate neurological disease/disorder, a set and/or range of stimulation protocols that requires the lowest voltage, and a protocol that maintains treatment efficacy over long periods of time, for example, the protocol can prevent habituation. Also, the protocol can be used to enhance a standard tonic and/or burst stimulus protocol such that both the non-topographic and the topographic systems are stimulated resulting in treatment of multiple symptoms, for example a patient having both pure tone and noise-like tinnitus and/or a patient having both pain and paresthesia.

The predetermined site for stimulation using tonic and burst stimulation can include, for example, peripheral neuronal tissue and/or central neuronal tissue. Peripheral neuronal tissue can include a nerve root or root ganglion or any peripheral neuronal tissue associated with a given dermatome or any neuronal tissue that lies outside the brain, brainstem or spinal cord. Peripheral nerves can include, but are not limited to olfactory nerve, optic nerve, oculomotor nerve, trochlear nerve, trigeminal nerve, abducens nerve, facial nerve, vestibulocochlear (auditory) nerve, glossopharyngeal nerve, vagal nerve, accessory nerve, hypoglossal nerve, occipital nerve (e.g., suboccipital nerve, the greater occipital nerve, the lesser occipital nerve), the greater auricular nerve, the lesser auricular nerve, the phrenic nerve, brachial plexus, radial axillary nerves, musculocutaneous nerves, radial nerves, ulnar nerves, median nerves, intercostal nerves, lumbosacral plexus, sciatic nerves, common peroneal nerve, tibial nerves, sural nerves, femoral nerves, gluteal nerves, thoracic spinal nerves, obturator nerves, digital nerves, pudendal nerves, plantar nerves, saphenous nerves, ilioinguinal nerves, gentofemoral nerves, and iliohypogastric nerves. Furthermore, peripheral neuronal tissue can include but is not limited to peripheral nervous tissue associated with a dermatome. An exemplary dermatome areas may comprise the C2/C3 dermatome area which comprises any peripheral nerve (e.g., the occipital nerve (the greater, the lesser, the third and the suboccipital nerve), the great auricular nerve, the transverse cervical nerve, the supraclavicular nerve, spinal accessory nerve, phrenic nerve, dorsal scapular nerve) that arises from the C2 or C3 nerve root. Central neuronal tissue includes brain tissue, spinal tissue or brainstem tissue. Brain tissue can include prefrontal cortex, dorsal lateral prefrontal cortex, auditory cortex, somatosensory cortex, thalamus/sub-thalamus, basal ganglia, hippocampus, amygdala, hypothalamus, mammilary bodies, substantia nigra or cortex or white matter tracts afferent to or efferent from the abovementioned brain tissue, inclusive of the corpus callosum, more particularly, the brain tissue includes the prefrontal cortex, auditory cortex and/or somatosensory cortex. Yet further, brain tissue can include various Brodmann Areas for example, but not limited to Brodmann Area 9, Brodmann Area 10, Brodmann Area 32, Brodmann Area 39, Brodmann Area 41, Brodmann Area 42, and Brodmann Area 46. Spinal tissue can include the ascending and descending tracts of the spinal cord, more specifically, the ascending tracts of that comprise intralaminar neurons or the dorsal column. For example, the spinal tissue can include neuronal tissue associated with any of the cervical vertebral segments (C1, C2, C3, C4, C5, C6, C7 and C8) and/or any tissue associated with any of the thoracic vertebral segments (T1, T2, T3, T4, T5, T6, T7, T8, T9, T10, T11, T12) and/or any tissue associated with any of the lumbar vertebral segments (L1, L2, L3, L4. L5, L6) and/or any tissue associated with the sacral vertebral segments (S1, S2, S3, S4, S5). More specifically, the spinal tissue is the dorsal column of the spinal cord. The brainstem tissue can include the medulla oblongata, pons or mesencephalon, more particular the posterior pons or posterior mesencephalon, Lushka's foramen, and ventrolateral part of the medulla oblongata.

Figure 4A:
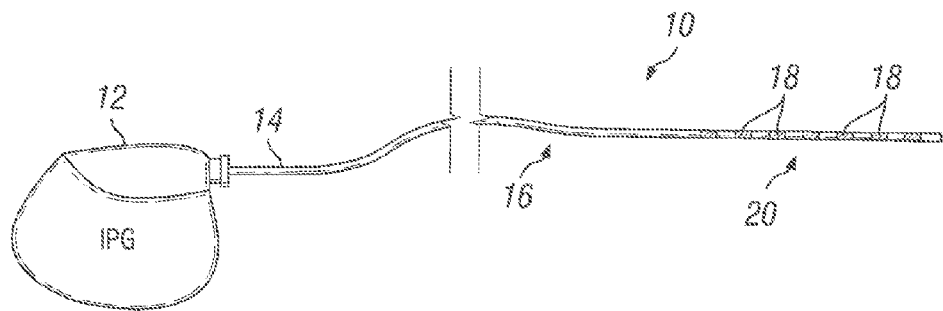
FIGS. 4A-4B illustrate an example stimulation system for electrically stimulating neuronal tissue.
Figure 4B:
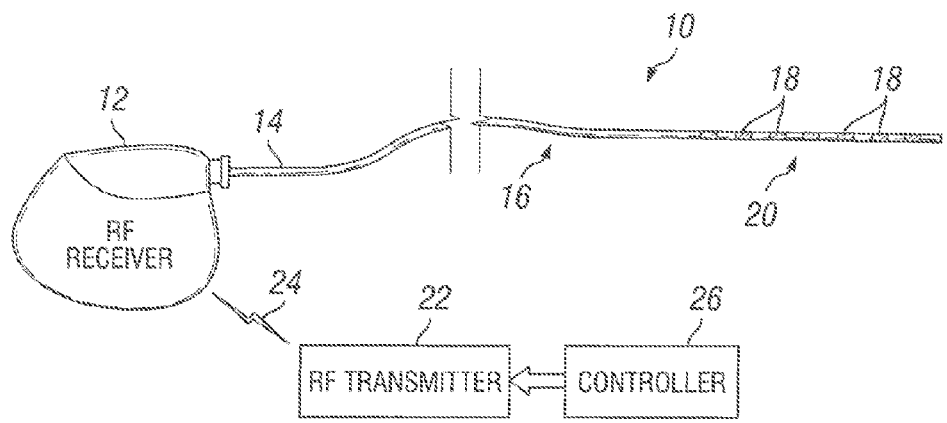

As described below, one or more stimulation leads 14, as shown in FIGS. 5A-5I, incorporated in stimulation system 10, as shown in FIGS. 4A and 4B, includes one or more electrodes 18 adapted to be positioned near the predetermined site or target tissue and used to deliver electrical stimulation energy to the predetermined site or target tissue in response to electrical signals received from stimulation source 12. Although various types of leads 14 are shown as examples, the present application contemplates stimulation system 10 including any suitable type of lead 14 in any suitable number and in any combination.

Medial or unilateral stimulation of the predetermined site may be accomplished using a single electrical stimulation lead 14 implanted in communication with the predetermined site, while bilateral electrical stimulation of the predetermined site may be accomplished using two stimulation leads 14 implanted in communication with the predetermined site on opposite sides of, for example, the spinal cord and or brain tissue. Multi-site implantation of stimulation leads can be used.

Implantation of Stimulation Lead with Stimulation Electrodes (800)

One or more stimulation leads 14, as shown in FIGS. 5A-5I are implanted such that one or more stimulation electrodes 18 of each stimulation lead 14 are positioned in communication with or in direct contact with or adjacent to the predetermined site. For the purposes described herein and as those skilled in the art will recognize, when an embedded stimulation system, such as the Bion®, is used, it is positioned similar to positioning the lead 14.

Techniques for implanting stimulation electrodes 18 are well known by those of skill in the art and may be positioned in various body tissues and in contact with various tissue layers; for example, deep brain, cortical, subdural, subarachnoid, epidural, cutaneous, transcutaneous and subcutaneous implantation is employed in some embodiments.

A. Brain

In certain embodiments, for example, patients who are to have an electrical stimulation lead or electrode implanted into the brain, generally, first have a stereotactic head frame, such as the Leksell, CRW, or Compass, mounted to the patient's skull by fixed screws. However, frameless techniques may also be used. Subsequent to the mounting of the frame, the patient typically undergoes a series of magnetic resonance imaging sessions, during which a series of two dimensional slice images of the patient's brain are built up into a quasi-three dimensional map in virtual space. This map is then correlated to the three dimensional stereotactic frame of reference in the real surgical field. In order to align these two coordinate frames, both the instruments and the patient must be situated in correspondence to the virtual map. The current way to do this is to rigidly mount the head frame to the surgical table. Subsequently, a series of reference points are established to relative aspects of the frame and patient's skull, so that either a person or a computer software system can adjust and calculate the correlation between the real world of the patient's head and the virtual space model of the patient MRI scans. The surgeon is able to target any region within the stereotactic space of the brain with precision (e.g., within 1 mm). Initial anatomical target localization is achieved either directly using the MRI images or functional imaging (PET or SPECTscan, fMRI, MSI), or indirectly using interactive anatomical atlas programs that map the atlas image onto the stereotactic image of the brain. As is described in greater detail elsewhere in this application, the anatomical targets or predetermined site may be stimulated directly or affected through stimulation in another region of the brain.

Based upon the coordinates, the electrical stimulation lead 14 can be positioned in the brain. Typically, an insertion cannula for electrical stimulation lead 14 is inserted through the burr hole into the brain, but a cannula is not required. For example, a hollow needle may provide the cannula. The cannula and electrical stimulation lead 14 may be inserted together or lead 14 may be inserted through the cannula after the cannula has been inserted.

Once electrical stimulation lead 14 has been positioned in the brain, lead 14 is uncoupled from any stereotactic equipment present, and the cannula and stereotactic equipment are removed. Where stereotactic equipment is used, the cannula may be removed before, during, or after removal of the stereotactic equipment. Connecting portion 16 of electrical stimulation lead 14 is laid substantially flat along the skull. Where appropriate, any burr hole cover seated in the burr hole may be used to secure electrical stimulation lead 14 in position and possibly to help prevent leakage from the burr hole and entry of contaminants into the burr hole.

Once electrical stimulation lead 14 has been inserted and secured, connecting portion 16 of lead 14 extends from the lead insertion site to the implant site at which stimulation source 12 is implanted. The implant site is typically a subcutaneous pocket formed to receive and house stimulation source 12. The implant site is usually positioned a distance away from the insertion site, such as near the chest, below the clavicle or alternatively near the buttocks or another place in the torso area. Once all appropriate components of stimulation system 10 are implanted, these components may be subject to mechanical forces and movement in response to movement of the person's body. A doctor, the patient, or another user of stimulation source 12 may directly or indirectly input signal parameters for controlling the nature of the electrical stimulation provided.

In addition to deep brain stimulation, cortical stimulation can also be used to stimulate various brain tissues, for example the auditory cortex. Various techniques for cortical stimulation are well known and used in the art, for example U.S. Pat. No. 7,302,298, which is incorporated herein by reference. The leads may be placed onto or directly into the target cortical tissue.

B. Spinal Cord and/or Peripheral Nerves

In certain embodiments, one or more stimulation electrodes 18 are positioned in communication with the neuronal tissue of the spinal cord. Stimulation electrodes 18 are commonly positioned external to the dura layer surrounding the spinal cord. Stimulation on the surface of the cord is also contemplated, for example, stimulation may be applied to the spinal cord tissue as well as to the nerve root entry zone. Stimulation electrodes 18 may be positioned in various body tissues and in contact with various tissue layers; for example, subdural, subarachnoid, epidural, and cutaneous, and/or subcutaneous implantation is employed in some embodiments.

Percutaneous leads commonly have two or more equally-spaced electrodes which are placed above the dura layer through the use of a Touhy-like needle. For insertion, the Touhy-like needle is passed through the skin between desired vertebrae to open above the dura layer. An example of an eight-electrode percutaneous lead is an OCTRODE® lead manufactured by Advanced Neuromodulation Systems, Inc. A Bion® stimulation system manufactured by Advanced Bionics Corporation is also contemplated. A percutaneous stimulation lead 14, such as example stimulation leads 14*a-d*, includes one or more circumferential electrodes 18 spaced apart from one another along the length of stimulating portion 20 of stimulation lead 14. Circumferential electrodes 18 emit electrical stimulation energy generally radially (i.e., generally perpendicular to the axis of stimulation lead 14) in all directions.

Figure 5A:
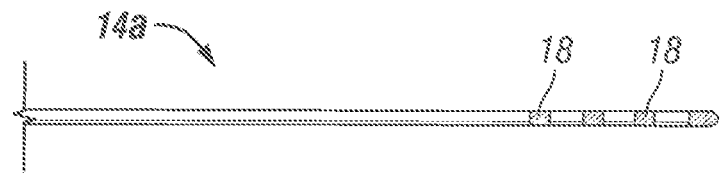
FIGS. 5A-5I illustrate example electrical stimulation leads that may be used to electrically stimulate neuronal tissue.
Figure 5B:
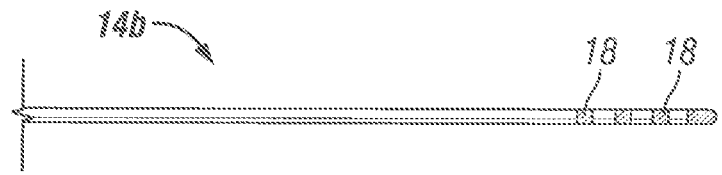
Figure 5C:
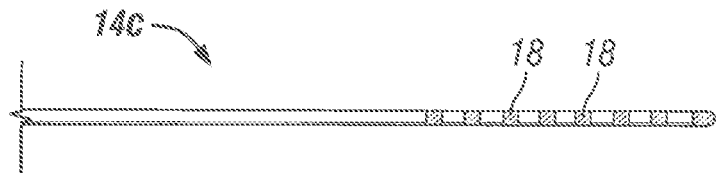
Figure 5D:
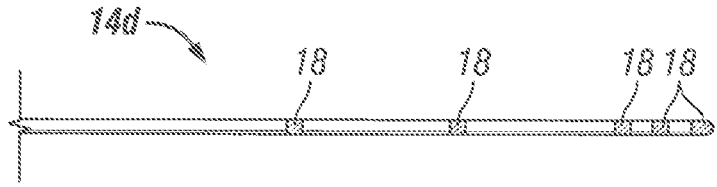
Figure 5E:
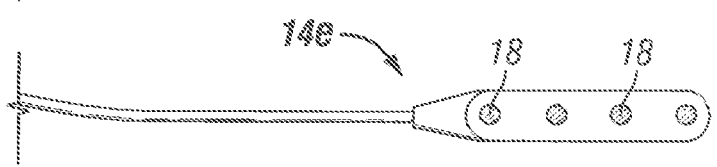
Figure 5F:
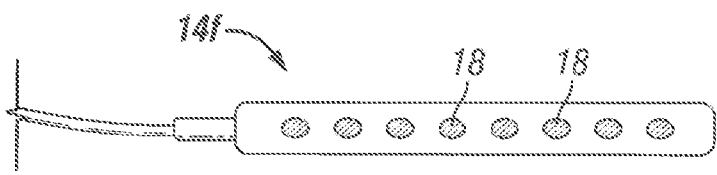
Figure 5G:
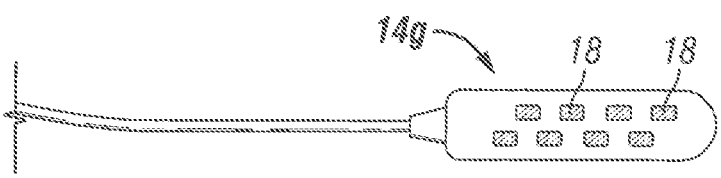
Figure 5H:
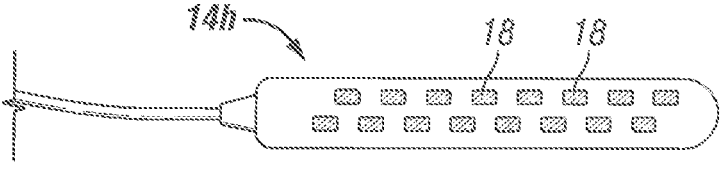
Figure 5I:
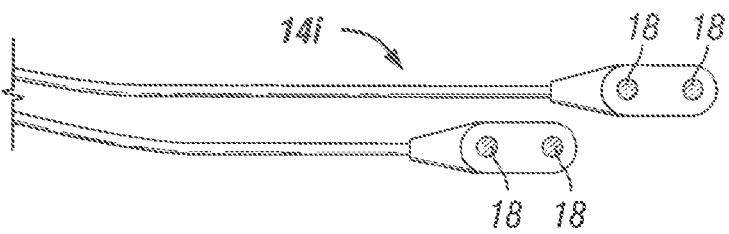

In contrast to the percutaneous leads, laminotomy leads have a paddle configuration and typically possess a plurality of electrodes (for example, two, four, eight, or sixteen) arranged in one or more columns. A laminotomy, paddle, or surgical stimulation lead 14, such as example stimulation leads 14*e-i*, includes one or more directional stimulation electrodes 18 spaced apart from one another along one surface of stimulation lead 14. Directional stimulation electrodes 18 emit electrical stimulation energy in a direction generally perpendicular to the surface of stimulation lead 14 on which they are located. An example of a sixteen-electrode laminotomy lead is shown in FIG. 5H. Another example of a laminotomy lead is an eight-electrode, two column laminotomy lead called the LAMITRODE® 44 lead, which is manufactured by Advanced Neuromodulation Systems, Inc. Implanted laminotomy leads are commonly transversely centered over the physiological midline of a patient. In such position, multiple columns of electrodes are well suited to address both unilateral and bilateral pain, where electrical energy may be administered using either column independently (on either side of the midline) or administered using both columns to create an electric field which traverses the midline. A multi-column laminotomy lead enables reliable positioning of a plurality of electrodes, and in particular, a plurality of electrode columns that do not readily deviate from an initial implantation position.

Laminotomy leads require a surgical procedure for implantation. The surgical procedure, or partial laminectomy, requires the resection and removal of certain vertebral tissue to allow both access to the dura and proper positioning of a laminotomy lead. The laminotomy lead offers a more stable platform, which is further capable of being sutured in place that tends to migrate less in the operating environment of the human body. Depending on the position of insertion, however, access to the dura may only require a partial removal of the ligamentum flavum at the insertion site. In some embodiments, two or more laminotomy leads may be positioned within the epidural space, and the leads may assume any relative position to one another.

C. Brainstem Stimulation

Implantation of a stimulation lead 14 in communication with the predetermined brainstem area can be accomplished via a variety of surgical techniques that are well known to those of skill in the art. For example, an electrical stimulation lead can be implanted on, in, or near the brainstem by accessing the brain tissue through a percutaneous route, an open craniotomy, or a burr hole. Where a burr hole is the means of accessing the brainstem, for example, stereotactic equipment suitable to aid in placement of an electrical stimulation lead 14 on, in, or near the brainstem may be positioned around the head. Another alternative technique can include, a modified midline or retrosigmoid posterior fossa technique.

In certain embodiments, electrical stimulation lead 14 is located at least partially within or below the dura mater adjacent the brainstem. Alternatively, a stimulation lead 14 can be placed in communication with the predetermined brainstem area by threading the stimulation lead up the spinal cord column, as described above, which is incorporated herein.

Yet further, a stimulation lead 14 can be implanted in communication with the predetermined brainstem area by a using stereotactic procedures similar to those described above, which are incorporated herein, for implantation via the cerebrum.

Still further, a predetermined brainstem area can be indirectly stimulated by implanting a stimulation lead 14 in communication with a cranial nerve (e.g., olfactory nerve, optic, nerve, oculomotor nerve, trochlear nerve, trigeminal nerve, abducent nerve, facial nerve, vestibulocochlear nerve, glossopharyngeal nerve, vagal nerve, accessory nerve, and the hypoglossal nerve) as well as high cervical nerves (cervical nerves have anastomoses with lower cranial nerves) such that stimulation of a cranial nerve indirectly stimulates the predetermined brainstem tissue. Such techniques are further described in U.S. Pat. Nos. 6,721,603; 6,622,047; and 5,335,657 each of which are incorporated herein by reference.

Coupling of Stimulation Source to Stimulation Lead (802)

In general terms, stimulation system 10 includes an implantable electrical stimulation source 12 and one or more implantable electrical stimulation leads 14 for applying electrical stimulation pulses to a predetermined site. In operation, both of these primary components are implanted in a subject's body, as discussed below. In certain embodiments, stimulation source 12 is coupled directly to a connecting portion 16 of stimulation lead 14. In other embodiments, stimulation source 12 is incorporated into the stimulation lead 14 and stimulation source 12 instead is embedded within stimulation lead 14. For example, such a stimulation system 10 may be a Bion® stimulation system manufactured by Advanced Bionics Corporation. Whether stimulation source 12 is coupled directly to or embedded within the stimulation lead 14, stimulation source 12 controls the stimulation pulses transmitted to one or more stimulation electrodes 18 located on a stimulating portion 20 of stimulation lead 14, positioned in communication with a predetermined site, according to suitable stimulation parameters (e.g., duration, amplitude or intensity, frequency, pulse width, etc.).

In one embodiment, as shown in FIG. 4, stimulation system 10 comprises implantable pulse generator (IPG) 12, stimulation lead 14, controller 26, and RF transmitter 24. IPG 12 typically comprises a metallic housing that encloses the pulse generating circuitry, control circuitry, communication circuitry, battery, recharging circuitry, etc. of the device. An example commercially available IPG is the EON® IPG available from Advanced Neuromodulation Systems, Inc. IPG 12 also typically comprises a header structure for electrically and mechanically coupling to stimulation lead 14. The electrical pulses generated by IPG 12 are conducted through conductors (not shown) embedded within stimulation lead 14 and delivered to tissue of the patient using electrodes 18 at distal end 20 of stimulation lead 14. In another embodiment, the IPG can be optimized for high frequency operation as described in U.S. Published Application No. US20060259098, which is incorporated herein by reference. Furthermore, IPG 12 may be adapted to communicate with external devices, such as controller 26, after implantation within a patient. For example, controller 26 may utilize RF transmitter 22 to conduct wireless communications 24 with IPG 12 after IPG 12 is implanted within a patient to control the operations of IPG 12. Specifically, a doctor, the patient, or another user may use a controller 26 located external to the person's body to provide control signals for operation of IPG 12. Controller 26 provides the control signals to wireless transmitter 22, wireless transmitter 22 transmits the control signals and power to the implanted pulse generator 12, and pulse generator 12 uses the control signals to vary the stimulation parameters of stimulation pulses transmitted through stimulation lead 14 to the predetermined spinal column site. Wireless transmitter 22 and controller 26 can be integrated within a single device and are commercially distributed with implantable pulse generator products.

Activate Stimulation Source and Transmit Stimulation Pulse (804)

Conventional neuromodulation devices can be modified to apply burst and tonic stimulation to nerve tissue of a patient by modifying the software instructions and/or stimulation parameters stored in the devices. Specifically, conventional neuromodulation devices typically include a microprocessor and a pulse generation module. The pulse generation module generates the electrical pulses according to a defined pulse width and pulse amplitude and applies the electrical pulses to defined electrodes. The microprocessor controls the operations of the pulse generation module according to software instructions stored in the device and accompanying stimulation parameters. An example of a commercially available neuromodulation device that can be modified or programmed to apply burst stimulation, as well as, tonic stimulation includes the EON®, manufactured by Advanced Neuromodulation Systems, Inc.

These conventional neuromodulation devices can be adapted by programming the microprocessor to deliver a number of spikes (relatively short pulse width pulses) that are separated by an appropriate inter-spike interval. Thereafter, the programming of the microprocessor causes the pulse generation module to cease pulse generation operations for an inter-burst interval. The programming of the microprocessor also causes a repetition of the spike generation and cessation of operations for a predetermined number of times. After the predetermined number of repetitions have been completed, the microprocessor can cause burst stimulation to cease for an amount of time and resume thereafter.

Yet further, the microprocessor can be programmed to cause a tonic spike pulse interspersed in or around the burst stimulus. Also, in some embodiments, the microprocessor could be programmed to cause the pulse generation module to deliver a hyperpolarizing pulse before the first spike of each group of multiple spikes.

The microprocessor can be programmed to allow the various characteristics of the burst stimulus to be set by a physician to allow the combination of the burst stimulus and tonic stimulus to be optimized to treat the patient's disease. For example, the spike amplitude, the inter-spike interval, the inter-burst interval, the number of bursts to be repeated in succession, the amplitude of the various pulses, the placement and/or timing of the tonic stimulus in relation to the burst stimulus, the amplitude of the tonic stimulus, the frequency of the tonic stimulus, the ratio of the burst stimulus to the tonic stimulus, altering the charge of the burst and/or tonic stimulus, altering the use of biopolar and/or unipolar or monopolar pulses (e.g., unipolar burst stimulus and bipolar tonic stimulus or bipolar burst stimulus and unipolar tonic stimulus) and other such characteristics could be controlled using respective parameters accessed by the microprocessor during burst stimulus and/or tonic stimulus operations. These parameters could be set to desired values by an external programming device via wireless communication with the implantable neuromodulation device.

Figure 6:
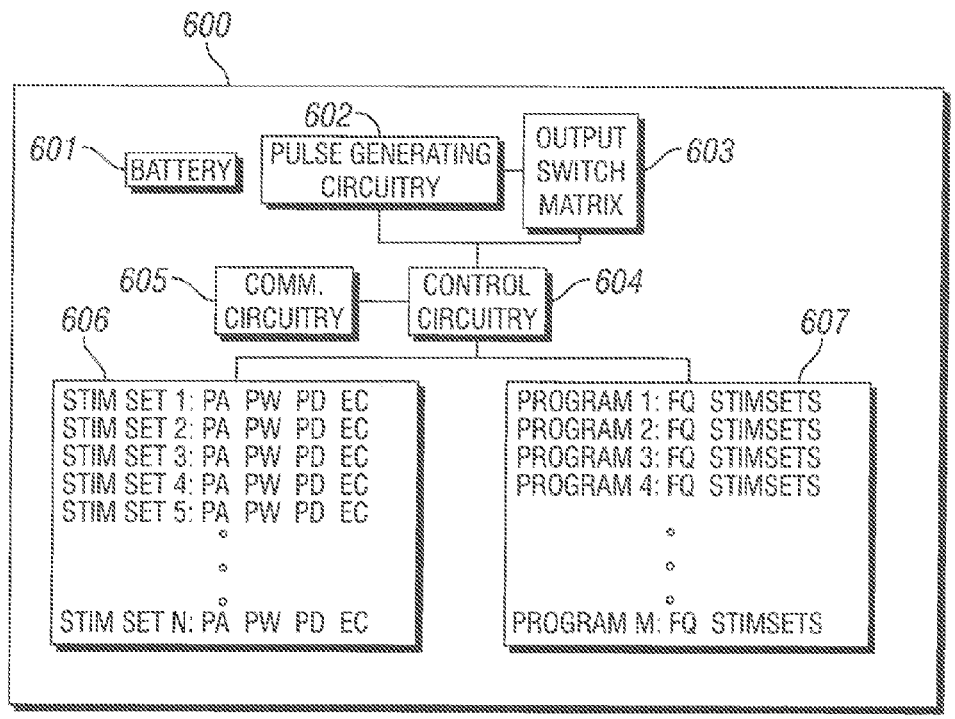
FIG. 6 depicts an implantable pulse generator that may be programmed to generate burst and tonic stimulation according to one representative embodiment.

FIG. 6 depicts a block diagram of IPG 600 that may be programmed to deliver burst and tonic stimulation in accordance with some representative embodiments. IPG 600 comprises battery 601, pulse generating circuitry 602, output switch matrix 603, control circuitry 604, and communication circuitry 605. Control circuitry 604 controls the generation of pulses by pulse generating circuitry 602 and the delivery of the generated pulses by output switch matrix 603. Specifically, control circuitry 604 controls the amplitude and pulse width of a respective pulse by controlling pulse generating circuitry 602. Additionally, control circuitry 604 controls the timing of the generation of pulses by controlling pulse generating circuitry 602. Control circuitry 604 further configures output switch matrix 603 to control the polarity associated with a plurality of outputs associated with switch matrix 603. In one representative embodiment, control circuitry 604 is implemented using a microprocessor and suitable software Instructions to implement the appropriate system control. Alternatively, control circuitry 604 may comprise an application specific integrated circuit.

Control circuitry 604 preferably controls pulse generating circuitry 602 and output switch matrix using "multi-stim set programs" which are known in the art. A "stim set" refers to a set of parameters which define a pulse to be generated. As shown in FIG. 6, a plurality of stim sets 606 are defined in memory of IPG 200. Each stim set defines a pulse amplitude, a pulse width, a pulse delay, and an electrode combination. The pulse amplitude refers to the amplitude for a given pulse and the pulse width refers to the duration of the pulse. The pulse delay represents an amount of delay to occur after the generation of the pulse (equivalently, an amount of delay could be defined to occur before the generation of a pulse). The amount of delay represents an amount of time when no pulse generation occurs. The electrode combination defines the polarities for each output of output switch matrix 603 which, thereby, controls how a pulse is applied via electrodes of a stimulation lead. Other pulse parameters could be defined for each stim set such as pulse type, repetition parameters, etc.

As shown in FIG. 6, IPG 600 comprises a plurality of stimulation programs 607. A stimulation program preferably defines a plurality of pulses to be generated in succession and the frequency of repetition of the pulses. Specifically, when control circuitry 604 executes a stimulation program, control circuitry 604 first retrieves the stimulation parameters for the first stimulation set of the stimulation program. Control circuitry 604 modifies an amplitude setting of pulse generating circuitry 602 according to the amplitude parameter of the stim set. Control circuitry 604 also configures output switch matrix 603 according to the electrode combination of the stim set. Then, control circuitry 604 causes pulse generating circuitry 602 to generate a pulse for an amount of time as defined by the pulse width parameter. Control circuitry 604 stops the pulse generation and waits an amount of time equal to the pulse delay parameter. Control circuitry 604 then proceeds to the next stimulation set in the stimulation program and repeats the process. Each stimulation set in the stimulation program is processed in the same manner. When the last stimulation set of the stimulation set is completed, control circuitry 604 waits an amount of time as defined by the frequency parameter of the stimulation program before beginning again. Then, control circuitry 604 generates another series of pulses according to the various stim sets. Thereby, a pulse is generated for each stim set according to the defined frequency of the stimulation program.

Figure 8:
FIG. 8 depicts a stimulation program for defining burst and tonic stimulation according to one representative embodiment.
Figure 7:
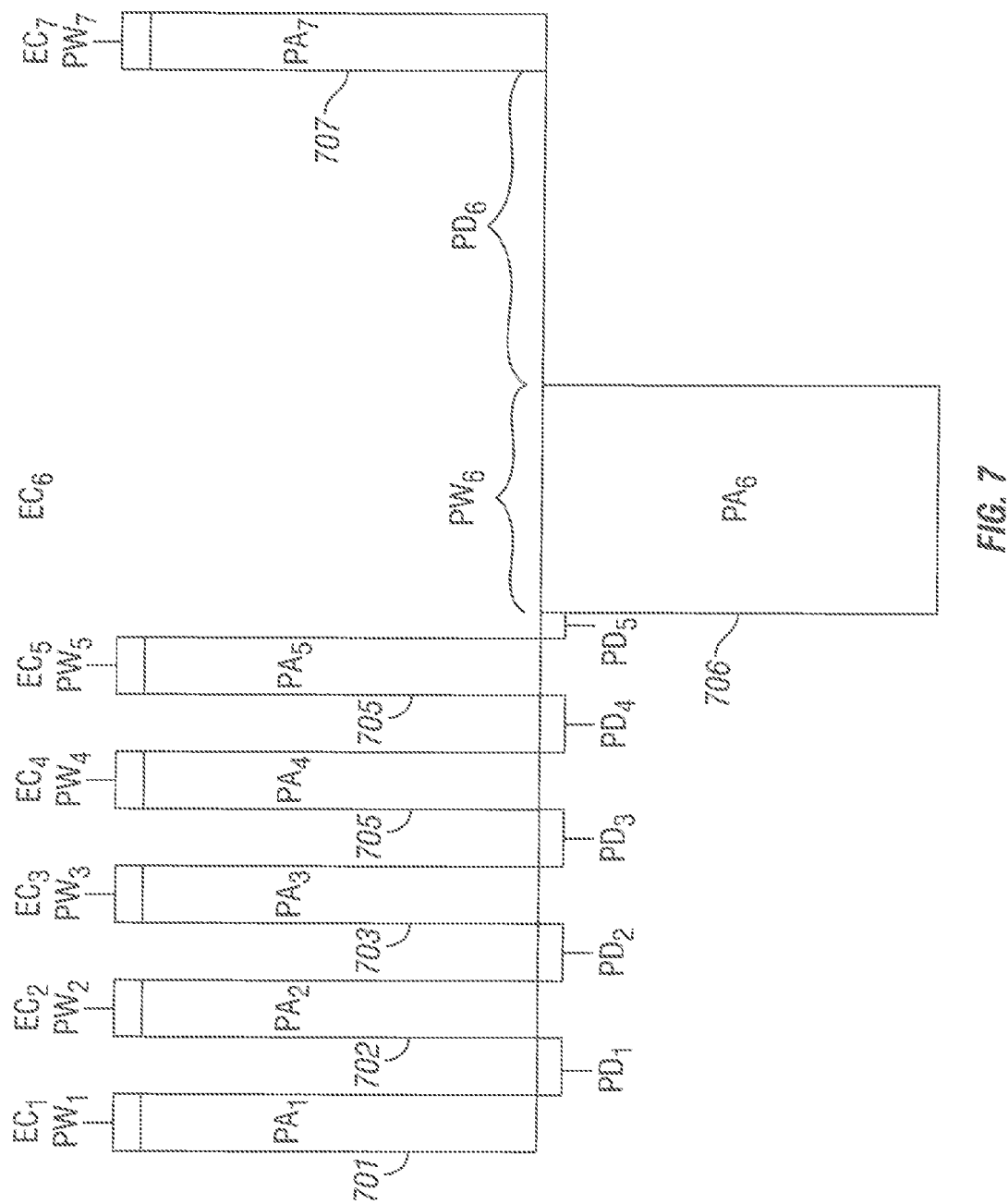
FIG. 7 depicts stimulation parameters for a number of pulses of burst and tonic stimulation according to one representative embodiment.

FIGS. 7 and 8 depict how stim sets and a stimulation program can be defined to generate burst and tonic stimulation according to one representative embodiment. FIG. 7 depicts a plurality of pulses 701-707. Pulses 701-705 are pulses of a discrete stimulation burst. The amplitude of pulses 701-705 can be defined in the amplitude parameters (shown as $PA_1$ through $PA_5$) of a plurality of stim sets. Each pulse lasts for an amount of time which is defined by the pulse width parameters of the plurality of stim sets (shown as $PW_1$ through $PW_5$). The pulses are output according the polarities of the electrode combinations (shown as $EC_1$ through $EC_5$) of the stim sets. Preferably, each electrode combination of the burst stimulus is the same. The inter-pulse or inter-spike intervals are defined by the delay parameters (shown as $PD_1$ through $PD_4$) of the stim sets.

A relatively small amount of delay is preferably defined to occur after the last pulse 705 of the burst stimulus before a charge balancing pulse 706 occurs (to permit settling in the circuits of IPG 600 before reversing polarity). The electrode combination (shown as $EC_6$) of the charging balancing pulse 706 is preferably the opposite of the electrode combination used for each pulse of the burst stimulus. That is, for each anode of the burst stimulus, the charging balancing pulse 706 will configure those outputs as cathodes (and vice versa). Another delay occurs after the charging balancing pulses 706 as defined by the delay parameter (shown as $PD_6$) for the respective stim set.

The last pulse 707 is a stimulation pulse for the tonic stimulation. The amplitude of the tonic stimulation pulse is defined by the amplitude parameter (shown as $PA_7$) of the respective stim set. The duration of the tonic stimulation pulse 707 is defined by the pulse width parameter (shown as $PW_7$) of the respective stim set. The tonic stimulation pulse is output according to the electrode combination of the respective stim set (shown as $EC_7$). The electrode combination of the tonic stimulation may be the same as the electrode combination for the burst stimulation or may differ from the electrode combination for the burst stimulation. The delay parameter for the last stim set is not shown. Any suitable value could be assigned to the last stim set as long as the delay value permits a stimulation program to be repeated at an appropriate frequency.

FIG. 8 depicts stimulation program 850 for the stimulation pattern shown in FIG. 7. Stimulation program 850 identifies stim sets SS1-SS7 as belonging to the stimulation program. Accordingly, when stimulation program 850 is executed by IPG 600, stimulation pulses will be successively generated according to the parameters of the stim sets. Stimulation program 850 defines the frequency for the stimulation program, in this case, 40 Hz (although any suitable frequency could be selected). The burst stimulus and the tonic stimulus as defined by these stim sets will be repeated according to the defined frequency parameter.

Referring again to FIG. 6, the parameters associated with the various stim sets and stimulation programs are preferably communicated to IPG 600 using communication circuitry 605. For example, an external programming device may communicate the various parameters of the stim sets to IPG 600. Then, the external programming device may communicate parameters defining a given stimulation program according to the created stim sets. It shall be appreciated that the parameters shown in FIGS. 6-8 are by way of example only. Other parameters may be utilized to define burst and/or tonic stimulation. For example, burst parameters could be communicated from the programming device to IPG 600 (e.g., burst amplitude, inter-pulse or inter-spike interval, intra-burst spike repetition rate, pulse number, etc.), and IPG 600 could automatically configure parameters in its internal memory or registers in response thereto.

In another embodiment, a neuromodulation device can be implemented to apply both burst and tonic stimulation using a digital signal processor and one or several digital-to-analog converters. The burst stimulus and/or tonic stimulus waveform could be defined in memory and applied to the digital-to-analog converter(s) for application through electrodes of the medical lead. The digital signal processor could scale the various portions of the waveform in amplitude and within the time domain (e.g., for the various intervals) according to the various burst and/or tonic parameters. A doctor, the patient, or another user of stimulation source 12 may directly or indirectly input stimulation parameters to specify or modify the nature of the stimulation provided.

In certain embodiments, the stimulation parameters may comprise a burst stimulation having a frequency in the range of about 1 Hz to about 300 Hz in combination with a tonic stimulation having a frequency in the range of about 1 Hz to about 300 Hz. Those of skill in the art realize that the frequencies can be altered depending upon the capabilities of the IPGs that are utilized. More particularly, the burst stimulation may be at about 6, 18, 40, 60, 80, 100, 150, 200, 250 or 300 Hz consisting of 5 spikes with 1 ms pulse width, 1 ms interspike interval in combination with about 6, 18, 40, 60, 80, 100, 150, 200, 250, 300 Hz tonic stimulation interspersed between or around the bursts, or any variation thereof depending upon the efficacy of treatment and the capabilities of the IPG.

Yet further, the initial stimulation protocol in step 804 can be a non-saturating stimulation protocol that only partially eliminates at least one symptom associated with the neurological disorder/disease. For example, a non-saturating protocol may be created by employing voltages or stimulation protocols known not to be completely effective in eliminating neurological disorder/disease. Using such non-saturating protocols, a location of maximum efficacy may be ascertained, with regards to the location of stimulation lead 14 and/or the differential activation of various stimulation electrodes 18. For example, a stimulation protocol may be designed for the patient at step 804 wherein a voltage is applied that only partially eliminate the neurological disorder/disease, and various stimulation parameters are tested in order to determine a protocol of maximum efficacy. Once an optimal location and protocol have been determined, the voltage or current may be adjusted to completely eliminate the neurological disorder/disease. In other embodiments, step 804 may include the application of a saturating stimulation protocol that reduces or alleviates the neurological disorder/disease. Similar to non-saturating protocols, saturating protocols can also be employed in step 804 such that the saturating stimulation protocol eliminates or alleviates at least one symptom associated with the neurological disorder/disease.

Still further, the initial stimulation protocol in step 804 may employ the use of either tonic and/or burst stimulation to determine the location of maximum efficacy with regards to the location of stimulation lead 14 and/or activation or various stimulation electrodes 18. Once the location of maximum efficacy is determined, then a stimulation protocol utilizing both tonic and burst stimulation can be employed to reduce or alleviate at least one symptom associated the neurological disorder/disease.

Trial Assessment (806)

In some embodiments, it is considered that several cycles of intra-implantation trials may be required. In preferred embodiments, a comparison of the patient's symptoms between multiple cycles of intra-implantation trial stimulation will be used to determine the optimal location and stimulation protocol. In further embodiments, steps 804 through 808 represent a repetitive cycle that ends when an optimal location and protocol have been selected. In some embodiments, once the stimulation lead 14 has been property positioned such that subject's symptoms are improved or absent, intra-implantation trial stimulation may be considered complete. It is contemplated that stimulation parameters may be modified to maximize the effectiveness of the therapy both prior to and subsequent to the end of the intra-implantation trial stimulations.

Those skilled in the art recognize that there are many methods to assess various improvements of symptoms associated with neurological disorders/diseases.

1. Tinnitus

A subject is administered a therapeutically effective stimulation so that the subject has an improvement in the parameters relating to tinnitus including informal questioning of the subject, formal subjective testing and analysis according to one or more audiology test, for example the Goebel tinnitus questionnaire or other validated tinnitus questionnaires, audiometry, tinnitus matching, impedence, BAEP, and OAE. The improvement is any observable or measurable improvement. Thus, one of skill in the art realizes that a treatment may improve the patient condition, but may not be a complete cure of the disease.

2. Pain

One example of a method for pain measurement is the use of the Visual Analog Scale (VAS). In the VAS patients are asked to rank their pain by making a mark on a bar that is labeled "no pain" on one end, and "pain as bad as possible" on the other end. Patients may mark the bar anywhere between the two opposite poles of perceived pain sensation. This mark can then be given any quantitative value such as fractional, decimal, or integer values by the clinician and used as a semi-quantitative pain measurement. In various tests for pain severity, patients may rank their pain on a scale between zero and ten, by a scale of faces depicting various emotions from happy to very sad and upset, and by answering a variety of questions describing the pain. In preferred embodiments, the patient's pain is assessed prior to and during the trial implantation procedure, for example prior to process 800, and then again at process 806. In other embodiments, informal subjective questioning of the person, and/or formal subjective testing and analysis may be performed to determine whether the subject's pain has sufficiently improved throughout the intra-implantation trial stimulation.

In addition to utilizing pain scores and grading and objective measures including use of additional pain medications (e.g., reduction in the amount of medication consume or elimination of the consumption of pain medications), other methods to determine improvement of a patient's pain may comprise administering various standardized questionnaires or tests to determine the patient's neuropsychological state.

3. Neuropsychological Tests

Thus, a subject is administered a therapeutically effective stimulation so that the subject has an improvement in the parameters relating to the neurological disorder or condition including subjective measures such as, for example, neurological examinations and neuropsychological tests (e.g., Minnesota Multiphasic Personality Inventory, Beck Depression Inventory, Mini-Mental Status Examination (MMSE), Hamilton Rating Scale for Depression, Wisconsin Card Sorting Test (WCST). Tower of London, Stroop task, MADRAS, CGI, N-BAC, or Yale-Brown Obsessive Compulsive score (Y-BOCS)), motor examination, and cranial nerve examination, and objective measures including use of additional psychiatric medications, such as anti-depressants, or other alterations in cerebral blood flow or metabolism and/or neurochemistry.

Patient outcomes may also be tested by health-related quality of life (HRQL) measures: Patient outcome measures that extend beyond traditional measures of mortality and morbidity, to include such dimensions as physiology, function, social activity, cognition, emotion, sleep and rest, energy and vitality, health perception, and general life satisfaction. (Some of these are also known as health status, functional status, or quality of life measures.)

In certain embodiments, in connection with improvement in one or more of the above or other neurological disorders, the electrical stimulation may have a "brightening" effect on the person such that the person looks better, feels better, moves better, thinks better, and otherwise experiences an overall improvement in quality of life.

Adjustment of Stimulation Parameters and/or Lead Location (808)

If the subject's neurological disorder/disease has not sufficiently improved at process 806, or if the reduction of the neurological disorder/disease is determined to be incomplete or inadequate during the intra-implantation trial stimulation procedure, stimulation lead 14 may be moved incrementally or even re-implanted, one or more stimulation parameters may be adjusted, or both of these modifications may be made at process 808 and the trial stimulation and analysis repeated until at least one symptom associated with the neurological disorder/disease has improved.

Implantation of Stimulation Source (810)

In some embodiments the intra-trial stimulation period is determined to be complete during process 806. In other embodiments, the intra-implantation trial stimulation is not performed, and the method proceeds from process 802 to 810. Once the location for the stimulation lead 14 has been determined, the stimulation lead may be properly implanted and secured and a stimulation source 12 may be surgically implanted at process 810. Techniques for implanting stimulation sources such as stimulation source 12 are known to those skilled in the art. For non-embedded systems, the implant site is typically a subcutaneous pocket formed to receive and house stimulation source 12. The implant site is usually located some distance away from the insertion site, such as in or near the lower back or buttocks.

Tunneling of Stimulation Lead to Stimulation Source (812)

Where stimulation lead 14 includes connecting portion 16, connecting portion 16 may be tunneled, at least in part, subcutaneously to the implant site of stimulation source 12 at step 812. Some embodiments may use a non-implantable stimulation source.

Input of Parameters to Stimulation Source (814)

During process 814, a doctor, the patient, or another user of stimulation source 12 may directly or indirectly input stimulation parameters for controlling the nature of the electrical stimulation provided to the target tissue area or predetermined area, if not already set during any intra-implantation trial stimulation period. If the method proceeds from 802 to 810, then the procedure for setting the parameters in step 814 follows the protocol as described above for step 804. Where appropriate, post-implantation trial stimulation may be conducted to determine the efficacy of various types of burst and tonic stimulation. Examples of efficacy metrics may include the minimum required voltage for a given protocol to achieve maximum and/or therapeutic benefits to the neurological disease and/or disorder. Efficacy metrics may also include a measurement of the presence and/or degree of habituation to a given protocol over one or more weeks or months, and any necessary modifications made accordingly. Such assessments can be conducted by suitable programming, such as that described in U.S. Pat. No. 5,938,690, which is incorporated by reference here in full. Utilizing such a program allows an optimal stimulation therapy to be obtained at minimal power. This ensures a longer battery life for the implanted systems.

In certain embodiments, it may be desirable for the patient to control the therapy to optimize the operating parameters to achieve increased or optimized the treatment. For example, the patient can alter the pulse frequency, pulse amplitude and pulse width using a hand held radio frequency device that communicates with the IPG. Once the operating parameters have been altered by the patient, the parameters can be stored in a memory device to be retrieved by either the patient or the clinician. Yet further, particular parameter settings and changes therein may be correlated with particular times and days to form a patient therapy profile that can be stored in a memory device.

Following post-implantation, the efficacy of the system can be determined by utilizing any of the any method well known and described to assess various improvements of symptoms associated with neurological disorders/diseases. Exemplary methods are described above under step 806 and incorporated herein by reference.

Although example steps are illustrated and described, the claimed material contemplates two or more steps taking place substantially simultaneously or in a different order. In addition, the claimed material contemplates using methods with additional steps, fewer steps, or different steps, so long as the steps remain appropriate for implanting stimulation system 10 into a person for electrical stimulation of the a predetermined site.

IV. Types of Neurological Conditions

Accordingly, the present application relates to modulation of neuronal activity to affect neurological, neuropsychological or neuropsychiatric activity. The present application finds particular application in the modulation of neuronal function or processing to affect a functional outcome. The modulation of neuronal function is particularly useful with regard to the prevention, treatment, or amelioration of neurological, psychiatric, psychological, conscious state, behavioral, mood, and thought activity (unless otherwise Indicated these will be collectively referred to herein as "neurological activity" which includes "psychological activity" or "psychiatric activity"). When referring to a pathological or undesirable condition associated with the activity, reference may be made to a neurological disorder which includes "psychiatric disorder" or "psychological disorder" instead of neurological activity or psychiatric or psychological activity. Although the activity to be modulated usually manifests itself in the form of a disorder such as a attention or cognitive disorders (e.g., Autistic Spectrum Disorders); mood disorder (e.g., major depressive disorder, bipolar disorder, and dysthymic disorder) or an anxiety disorder (e.g., panic disorder, posttraumatic stress disorder, obsessive-compulsive disorder and phobic disorder); neurodegenerative diseases (e.g., multiple sclerosis, Alzheimer's disease, amyotrophic lateral sclerosis (ALS), Parkinson's disease, Huntington's Disease, Guillain-Barre syndrome, myasthenia gravis, and chronic idiopathic demyelinating disease (CID)), movement disorders (e.g, dyskinesia, tremor, dystonia, chorea and ballism, tic syndromes, Tourette's Syndrome, myoclonus, drug-induced movement disorders, Wilson's Disease, Paroxysmal Dyskinesias, Stiff Man Syndrome and Akinetic-Ridgid Syndromes and Parkinsonism), epilepsy, tinnitus, pain, phantom pain, diabetes neuropathy, one skilled in the art appreciates that some methods of treatment may also find application in conjunction with enhancing or diminishing any neurological or psychiatric function, not just an abnormality or disorder. Neurological activity that may be modulated can include, but not be limited to, normal functions such as alertness, conscious state, drive, fear, anger, anxiety, repetitive behavior, impulses, urges, obsessions, euphoria, sadness, and the fight or flight response, as well as instability, vertigo, dizziness, fatigue, photofobia, concentration dysfunction, memory disorders, headache, dizziness, irritability, fatigue, visual disturbances, sensitivity to noise (misophonia, hyperacusis, phonofobia), judgment problems, depression, symptoms of traumatic brain injury (whether physical, emotional, social or chemical), autonomic functions, which includes sympathetic and/or parasympathetic functions (e.g., control of heart rate), somatic functions, and/or enteric functions. Thus, the present application encompasses modulation of central and/or peripheral nervous systems.

Other neurological disorders can include, but are not limited to headaches, for example, migraine, trigeminal autonomic cephalgia (cluster headache (episodic and chronic)), paroxysmal hemicrania (epidsodic and chronic), hemicrania continua, SUNCT (shortlasting unilateral neuralgiform headache with conjunctival injection and tearing), cluster tic syndrome, trigenminal neuroalgia, tension type headache, idiopathic stabbing headache, etc. The neurostimulation device can be implanted intracranially or peripherally, for example, but not limited to implanting a neurostimulation device occipitally for the treatment of headaches.

Autonomic and/or enteric nervous system disorders that can be treated using the stimulation system and/or certain representative methods of treatment include, but are not limited to hypertension, neurosis cordis or heart rhythm disorders, obesity, gastrointestinal motion disorders, respiratory disorders, diabetes, sleep disorders, snoring, incontinence both urologic and gastrointestinal, sexual dysfunction, chronic fatigue syndrome, fibromyalgia, whiplash associated symptoms, post-concussion syndrome, posttraumatic stress disorder etc.

Yet further immunological disorders may also be treated using the stimulation system and/or representative methods of treatment. This is based on the fact that the immune system senses antigens coordinates metabolic, endocrine and behavioral changes that support the immune system and modulates the immune system via neuroendocrine regulation and direct immune cell regulation. Such immunological disorders include, such as allergy, rhinitis, asthma, rheumatoid arthritis, psoriasis arthritis, lupus erythematosus disseminatus, multiple sclerosis and other demyelinating disorders, autoimmune thyroiditis, Crohn's disease, diabetis melitus etc.

Yet further tumoral disorders, both malignant and benign may also be treated using the stimulation system and/or some representative methods of treatment. This is based on the fact that tumoral behavior is linked to immunological function. This is seen in immunodeficiency syndromes such as AIDS and hematological disorders, where multiple and different tumors develop. In this setting neuromodulation could indirectly influence tumoral behavior.

Yet further neuroendocrine disorders may also be treated using the stimulation system and/or some representative methods of treatment. Such disorders are stress reactions, hypothalamic-pituitary axis dysfunction, etc.

Yet further functional disorders may also be treated using the stimulation system and/or some representative methods of treatment. Such disorders can be anorexia, boulemia, phobias, addictions, paraphilia, psychosis, depression, bipolar disorder, kleptomania, aggression, or antisocial sexual behavior. One skilled in the art appreciates that some representative embodiments may also find application in conjunction with enhancing or diminishing any neurological or psychiatric function, not just an abnormality or disorder.

Some representative neuromodulation methods of treatment can be used to alter a physiological and/or pathological signaling pattern. Thus, it is envisioned that the stimulation method as used herein can alter such patterns to alleviate the neurological condition or disease, or to improve or enhance a desired physiological function (e.g., self confidence, alleviating shyness, distrust etc).

In certain embodiments, the neuromodulation method can be used to treat neurological disorders or diseases that result from incorrect central nervous system control in which the disorder comprises a regular bursting rhythm. Such disorders having a regular bursting rhythm include, but are not limited to Parkinson's, epilepsy, tinnitus and phantom pain or other forms of deafferentation or central pain. Thus, it is envisioned that some representative methods of neuromodulation will alter or disrupt the regular bursting rhythm associated with the disorder.

Still further, it is known that the sympathetic system fires in bursts, and the parasympathetic system as well. Any neurological or non-neurological disorder associated with a hypoactive, hyperactive or maladaptive sympathetic or parasympathetic firing can be modified using this method.

Still further, the neuromodulation method can be used to treat neurological disorders or diseases that result from incorrect central nervous system control in which the disorder comprises an irregular bursting rhythm. Such disorders can include, but are not limited to dystonia or chorea or hallucinations. Thus, it is envisioned that such conditions are caused or linked to arrhythmic burst firing or desynchronized tonic firing can be treated utilizing some representative neuromodulation systems and/or stimulation parameters.

In different motor, sensory and autonomic neurological disorders two mechanisms might be involved: the firing rate is altered in tonic and burst firing cells and the amount of burst firing is increased. A second mechanism involved is an alteration in the synchrony of neuronal firing, which is often increased.

REFERENCES CITED

All patents and publications mentioned in the specifications are indicative of the levels of those skilled in the art. All patents and publications are herein incorporated by reference to the same extent as if each individual publication was specifically and individually indicated to be incorporated by reference.

U.S. Application No. 60/528,604
U.S. Application No. 60/528,689
U.S. Pat. No. 5,335,657
U.S. Pat. No. 5,938,690
U.S. Pat. No. 6,567,696
U.S. Pat. No. 6,622,047
U.S. Pat. No. 6,671,555
U.S. Pat. No. 6,690,974
U.S. Pat. No. 6,721,603
U.S. Pat. No. 6,740,072
U.S. Pat. No. 6,748,276
Alain, C., D. L. Woods, et al., (1998). Brain Res 812(1-2): 23-37.
Alho, K. (1995). Ear Hear 16(1): 38-51.
Bandrowski, A. E., S. L. Moore, et al., (2002). Synapse 44(3): 146-57.
Beurrier, C., P. Congar, et al., (1999). J Neurosci 19(2): 599-609.
Binder, Adv Exp Med Biol. 2004; 548:34-56.

Brozoski, T. J., C. A. Bauer, et al., (2002). J Neurosci 22(6): 2383-90.
Brumberg, The Journal of Neuroscience, 20 (13):4829-4843), 2000
Brumberg, The Journal of Neuroscience, Jul. 1, 2000, 20(13):4829-4843.
Cazals, Y., K. C. Homer, et al., (1998). J Neurophysiol 80(4): 2113-20.
Chen, G. D. and P. J. Jastreboff (1995). Hear Res 82(2): 158-78.
Chemigovskii, V. N., S. S. Musyashchikova, et al., (1979). Biol Bull Acad Sci USSR 6(1): 1-7.
Condon, C. D. and N. M. Weinberger (1991). Behav Neurosci 105(3): 416-30.
Cooper, D. C. (2002). Neurochem Int 41(5): 333-40.
Coro, F., P. E. M, et al., (1998). J Exp Biol 201(Pt 20): 2879-2890.
Coutinho, V. and T. Knopfel (2002). Neuroscientist 8(6): 551-61.
De Ridder, D., G. De Mulder, et al. (2005). ORL in press.
De Ridder, D., E. Verstraeten, et al. (2005). Otol Neurotol 26(4): 616-619.
De Ridder, D. et al., (2007a). Int. J. Med. Sci. 2007 4(5): 237-241.
De Ridder, D. et al., (2007b). Int. J. Med. Sci. 2007 4(5):242-246.
Huang, Y. Z., M. J. Edwards, et al. (2005). Neuron 45(2): 201-6.
Plewnia, C., M. Bartels, et al. (2003). Ann Neurol 53(2): 263-6.
Csepe, V., G. Karmos, et al., (1987). Electroencephalogr Clin Neurophysiol 66(6): 571-8.
Deouell, L. Y., S. Bentin, et al., (1998). Psychophysiology 35(4): 355-65.
Diamond, D. M. and N. M. Weinberger (1984). Behav Neurosci 98(2): 189-210.
Disney, A. and M. B. Calford (2001). J Neurophysiol 86(2): 1052-6.
Edeline, J. M., N. Neuenschwander-el Massioui, et al., (1990). Behav Brain Res 39(2): 145-55.
Edeline, J. M., Y. Manunta, et al., (2000). J Neurophysiol 84(2): 934-52.
Eggermont, J. J. (1990). Hear Res 48(1-2): 111-23.
Eggermont, J. J. (2003). Auris Nasus Larynx 30 Suppl: S7-12.
Eggermont, J. J. and M. Kenmochi (1998). Hear Res 117 (1-2): 149-60.
Fairhall, A. L., G. D. Lewen, et al., (2001). Nature 412 (6849): 787-92.
Feig, S. L. (2004). J Comp Neurol 468(1): 96-111.
Fischer, C., D. Moret, et al., (2000). Audiol Neurootol 5(3-4): 192-7.
Franceschetti et al., Brain Res. 1995 Oct. 23; 696(1-2):127-39.
Futatsugi, Y. and J. J. Riviello, Jr. (1998). Brain Dev 20(2): 75-9.
Gerken, G. M. (1996). Hear Res 97(1-2): 75-83.
Givois, V. and G. S. Pollack (2000). J Exp Biol 203 Pt 17: 2529-37.
Gopal, K. V. and G. W. Gross (2004). Hear Res 192(1-2): 10-22.
Gray and Singer, Proc Natl Acad Sci USA. 1989 March; 86(5):1698-702.
Guatteo et al., Brain Res. 1996 Nov. 25; 741(1-2):1-12.
He, J. (1997). J Neurophysiol 77(2): 896-908.
He, J. (2003). Exp Brain Res 153(4): 579-90.
He, J. and B. Hu (2002). J Neurophysiol 88(4): 2152-6.
He, J., Y. Q. Yu, et al., (2002). J Neurophysiol 88(2): 1040-50.
Hsieh, C. Y., S. J. Cruikshank, et al., (2000). Brain Res 880(1-2): 51-64.
Hu, B. (1995). J Physiol 483 (Pt 1): 167-82.
Hu, B., V. Senatorov, et al., (1994). J Physiol 479 (Pt 2): 217-31.
Huguenard, J. R. (1999). Adv Neurol 79: 991-9.
Jastreboff, P. J. (1990). Neurosci Res 8(4): 221-54.
Jastreboff, P. J. and C. T. Sasaki (1986). J Acoust Soc Am 80(5): 1384-91.
Jastreboff, P. J., J. F. Brennan, et al., (1988). Laryngoscope 98(3): 280-6.
Javitt, D. C., M. Steinschneider, et al., (1994). Brain Res 667(2): 192-200.
Javitt, D. C., M. Steinschneider, et al., (1996). Proc Nati Acad Sci USA 93(21): 11962-7.
Jeanmonod, D., M. Magnin, et al., (1996). Brain 119 (Pt 2): 363-75.
Joliot et al., Proc Natl Acad Sci USA. 1994 Nov. 22; 91(24):11748-51.
Jongsma, M. L., C. M. Van Rijn, et al., (1998). Eur J Pharmacol 341(2-3): 153-60.
Kaltenbach, J. A. and C. E. Afman (2000). Hear Res 140(1-2): 165-72.
Kaltenbach, J. A., D. A. Godfrey, et al., (1998). Hear Res 124(1-2): 78-84.
Kaltenbach, J. A., M. A. Zacharek, et al., (2004). Neurosci Lett 355(1-2): 121-5.
Kawaguchi, Y. and Y. Kubota (1993). J Neurophysiol 70(1): 387-96.
Kelly, J. B. and H. Zhang (2002). Hear Res 168(1-2): 35-42.
Kepecs, A. and J. Lisman (2003). Network 14(1): 103-18.
Kepecs, A., X. J. Wang, et al., (2002). J Neurosci 22(20): 9053-62.
Kraus, N., T. McGee, et al., (1992). Ear Hear 13(3): 158-64.
Kraus, N., T. McGee, et al., (1994). J Neurophysiol 72(3): 1270-7.
LeDoux, J. E., A. Sakaguchi, et al., (1984). J Neurosci 4(3): 683-98.
Lee et al., J Neurosci. 2001 Mar. 1; 21(5):1757-66.
Lever et al., J Neurosci. 2001 Jun. 15; 21(12):4469-77.
Lisman, J. E. (1997). Trends Neurosci 20(1): 38-43.
Ma, C. L., J. B. Kelly, et at, (2002). Hear Res 168(1-2): 25-34.
Martin, W. H., J. W. Schwegler, et al., (1993). Laryngoscope 103(6): 600-4.
Massaux, A. and J. M. Edeline (2003). Exp Brain Res 153(4): 573-8.
Massaux, A., G. Dutrieux, et al., (2004). J Neurophysiol 91(5): 2117-34.
Mattia et al., Hippocampus. 1997; 7(1):48-57.
Matveev, Cerebral Cortex, Vol. 10, No. 11, 1143-1153, November 2000.
McAlonan and Brown, Neuroscientist. 2002 August; 8(4): 302-5.
McCormick, D. A. and H. R. Feeser (1990). Neuroscience 39(1): 103-13.
McCormick, D. A. and M. von Krosigk (1992). Proc Nati Acad Sci USA 89(7): 2774-8.
Miller, L. M., M. A. Escabi, et al., (2001). J Neurosci 21(20): 8136-44.
Miller, L. M., M. A. Escabi, et al., (2001). Neuron 32(1): 151-60.
Moller, A. R. (1984). Ann Otol Rhinol Laryngol 93(1 Pt 1): 39-44.

Mooney, D. M., L. Zhang, et al., (2004). Proc Natl Acad Sci USA 101(1): 320-4.
Muller, J. R., A. B. Metha, et al., (1999). Science 285(5432): 1405-8.
N. Urbain, et al., J. Neurosci., Oct. 1, 2002; 22(19): 8665-8675
Naätanen, R. (1992). Attention and brain function. Hillsdale, N.J., Lawrence Erlbaum.
Naatanen, R. (2001). Psychophysiology 38(1): 1-21.
Naatanen, R., P. Paavilainen, et al., (1993). Psychophysiology 30(5): 436-50.
Nousak, J. M., D. Deacon, et al., (1996). Brain Res Cogn Brain Res 4(4): 305-17.
Ochi, K. and J. J. Eggermont (1996). Hear Res 95(1-2): 63-76.
Ochi, K. and J. J. Eggermont (1997). Hear Res 105(1-2): 105-18.
Ohzawa, I., G. Sclar, et al., (1985). J Neurophysiol 54(3): 651-67.
Oleskevich, S. and B. Walmsley (2002). J Physiol 540(Pt 2): 447-55.
Pantev, C., H. Okamoto, et al., (2004). Eur J Neurosci 19(8): 2337-44.
Perez-Reyes, E. (2003). Physiol Rev 83(1): 117-61.
Poremba, A., D. Jones, et al., (1998). Eur J Neurosci 10(10): 3035-43.
Puel, J. L. (1995). Prog Neurobiol 47(6): 449-76.
Puel, J. L., J. Ruel, et al., (2002). Audiol Neurootol 7(1): 49-54.
Ramcharan, E. J., C. L. Cox, et al., (2000). J Neurophysiol 84(4): 1982-7.
Ritter, W., D. Deacon, et al., (1995). Ear Hear 16(1): 52-67.
Romanski, L. M. and J. E. LeDoux (1992). J Neurosci 12(11): 4501-9.
Sakurai, Y. (1990). Behav Neurosci 104(2): 253-63.
Sakurai, Y. (2002). Neuroscience 115(4): 1153-63.
Sanes, D. H., J. McGee, et al., (1998). J Neurophysiol 80(1): 209-17.
Schwarz, D. W., F. Tennigkeit, et al., (2000). Acta Otolaryngol 120(2): 251-4.
Schwindt and Crill, J Neurophysiol. 1999 March 81(3): 1341-54.
Sherman, S. M. (2001). Nat Neurosci 4(4): 344-6.
Sherman and Guillery, Neuron. 2002 Jan. 17; 33(2):163-75.
Sherman and Guillery, Philos Trans R Soc Lond B Biol Sci. 2002 Dec. 29; 357(1428): 1695-708.
Sherman and Guillery, Philos Trans R Soc Lond B Biol Sci. 2002 Dec. 29; 357(1428):1809-21.
Sherman, S. M. (2001). Trends Neurosci 24(2): 122-6.
Steriade, M. and R. R. Llinas (1988). Physiol Rev 68(3): 649-742.
Steriade, M., D. Pare, et al., (1989). J Neurosci 9(7): 2215-29.
Steriade, Neuroscience. 2000; 101(2):243-76.
Suga, N., Y. Zhang, et al., (1997). J Neurophysiol 77(4): 2098-114.
Swadlow, H. A. and A. G. Gusev (2001). Nat Neurosci 4(4): 402-8.
Tabak, J. and P. E. Latham (2003). Neuroreport 14(11): 1445-9.
Tennigkeit, F., D. W. Schwarz, et al., (1996). J Neurophysiol 76(6): 3597-608.
Tennigkeit, F., E. Pull, et al., (1997). Acta Otolaryngol 117(2): 254-7.
Tiitinen, H., K. Alho, et al., (1993). Psychophysiology 30(5): 537-40.
Traub et al., J Physiol. 1994 Nov. 15; 481 (Pt 1):79-95.
Ulanovsky, N., L. Las, et al., (2003). Nat Neurosci 6(4): 391-8.
van Vreeswijk, C. and D. Hansel (2001). Neural Comput 13(5): 959-92.
Wan et al., Neuroscience. 2004; 125(4):1051-60.
Webster, W. R. (1971). Electroencephalogr Clin Neurophysiol 30(4): 318-30.
Weinberger, N. M. (1998 Neurobiol Learn Mem 70(1-2): 226-51.
Weinberger, N. M. (2004). Nat Rev Neurosci 5(4): 279-90.
Weinberger, N. M. and J. S. Bakin (1998). Audiol Neurootol 3(2-3): 145-67.
Wong and Stewart, J Physiol. 1992 November; 457:675-87.
Wu, S. H., C. L. Ma, et al., (2004). J Neurosci 24(19): 4625-34.
Zacharek, M. A., J. A. Kaltenbach, et al., (2002). Hear Res 172(1-2): 137-43.
Zhang, J. S. and J. A. Kaltenbach (1998). Neurosci Lett 250(3): 197-200.
Zhang, Y., N. Suga, et al., (1997). Nature 387(6636): 900-3.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

What is claimed is:

1. A method of treating chronic pain in a patient with reduced paresthesia, the method comprising:
   storing, in an implantable pulse generator, burst stimulation parameters that define stimulation pulses to be repeated in bursts, wherein the burst stimulation parameters include a pulse repetition frequency of at least 200 Hz, a burst rate of at least 18 Hz, and a pulse width of approximately 1 ms;
   generating, by the implantable pulse generator, burst stimulation according to the stimulation parameters, wherein the burst stimulation includes a plurality of bursts with each burst Including a plurality of pulses having the pulse width repeating at the pulse repetition frequency followed by quiescent periods such that bursts within the plurality of bursts repeat at the burst rate;
   providing the burst stimulation from the implantable pulse generator to a stimulation lead; and
   applying the burst stimulation to nerve tissue of the patient via one or more electrodes of the stimulation lead, wherein the burst stimulation causes the patient to experience pain relief with reduced paresthesia.

2. The method of claim 1 wherein the applying applies the burst stimulation to the spinal cord of the patient.

3. The method of claim 1 wherein the applying applies the burst stimulation to a dorsal root ganglion of the patient.

4. The method of claim 1 wherein each burst of the plurality of bursts includes at least five (5) pulses.

* * * * *